US009848846B2

United States Patent
Zhou

(10) Patent No.: US 9,848,846 B2
(45) Date of Patent: Dec. 26, 2017

(54) SYSTEMS AND METHODS FOR DETERMINING RADIATION DOSE IN COMPUTED TOMOGRAPHY SCANS

(71) Applicant: Cedars-Sinai Medical Center, Los Angeles, CA (US)

(72) Inventor: Yifang Zhou, Irvine, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 155 days.

(21) Appl. No.: 14/910,314

(22) PCT Filed: Aug. 4, 2014

(86) PCT No.: PCT/US2014/049647
§ 371 (c)(1),
(2) Date: Feb. 5, 2016

(87) PCT Pub. No.: WO2015/020981
PCT Pub. Date: Feb. 12, 2015

(65) Prior Publication Data
US 2016/0166224 A1  Jun. 16, 2016

Related U.S. Application Data

(60) Provisional application No. 61/862,415, filed on Aug. 5, 2013, provisional application No. 62/026,459, filed on Jul. 18, 2014.

(51) Int. Cl.
*A61B 6/03* (2006.01)
*A61B 6/00* (2006.01)
(52) U.S. Cl.
CPC ............. *A61B 6/542* (2013.01); *A61B 6/032* (2013.01); *A61B 6/583* (2013.01)

(58) Field of Classification Search
CPC .. A61B 6/00; A61B 6/03; A61B 6/032; A61B 6/542; A61B 6/583; A61B 6/54; A61B 6/544; G01N 23/046
(Continued)

(56) References Cited

U.S. PATENT DOCUMENTS

| 5,661,773 A | 8/1997 | Swerdloff et al. |
| 2005/0031082 A1 | 2/2005 | Haaga et al. |

(Continued)

FOREIGN PATENT DOCUMENTS

WO   2013049818 A1   4/2013

OTHER PUBLICATIONS

Aldrich, J.E. et al., Radiation dose in abdominal computed tomography: The role of patient size and the selection of tube current; JACR, 2006, 57(3):152-158.

(Continued)

*Primary Examiner* — Jurie Yun
(74) *Attorney, Agent, or Firm* — Linda B. Huber; Nixon Peabody LLP

(57) ABSTRACT

Systems and methods are described for determining a minimum radiation dose for a computed tomography (CT) scanning device. The method includes receiving a first input indicative of a selected minimum detectable contrast and a second input indicative of an estimate of a size of a subject to be exposed to the radiation dose. A minimum radiation dose to be applied via a radiation source is determined. The minimum radiation dose is determined at least in part by a power law model relating the size of the subject, a lesion size, and a minimum detectable contrast. The power law model is defined as MDC=A(L) $d^{B(L)}$ Dose$^{C(L)}$, wherein (i) MDC is the selected minimum detectable contrast, (ii) d is lesion size, (iii) Dose is radiation dose, (iv) A(L), B(L), and (Continued)

C(L) are pre-determined fitted parameters, and (v) L is the estimate of the size of the subject.

21 Claims, 39 Drawing Sheets

(58) Field of Classification Search
USPC .......................... 378/4, 8, 16, 18, 108, 901
See application file for complete search history.

(56) References Cited

U.S. PATENT DOCUMENTS

| | | |
|---|---|---|
| 2012/0002781 A1 | 1/2012 | Graham et al. |
| 2012/0230576 A1 | 9/2012 | Rohler et al. |
| 2013/0101079 A1 | 4/2013 | Hough et al. |

OTHER PUBLICATIONS

Ngaile, J.E. et al., Patient-size-dependent radiation dose optimisation technique for abdominal CT examinations, Radiation Protection Dosimetry, 2012, 148(2):189-201.

Zatelli, G. et al., A study of feasibility of dose reduction in paediatric MSCT scanning with a constant image quality, Physica Medica, 2008, 24(2):107-111.

International Search Report and Written Opinion dated Apr. 1, 2015 for International Application No. PCT/US14/49647 filed Aug. 4, 2014, 10 pages.

FIG. 4

| MODEL NO. | AGE GROUP | PA DIAMETER | LR DIAMETER | THICKNESS |
|---|---|---|---|---|
| 007TE-01 | Abdominal - Newborn | 9.0 cm | 10.5 cm | 15.0 cm |
| 007TE-02 | Abdominal - 1 year old | 11.5 cm | 14.0 cm | 15.0 cm |
| 007TE-03 | Abdominal - 5 year old | 14.0 cm | 18.0 cm | 15.0 cm |
| 007TE-04 | Abdominal - 10 year old | 16.0 cm | 20.5 cm | 15.0 cm |
| 007TE-06 | Abdominal - Small Adult | 22.0 cm | 30.0 cm | 15.0 cm |
| 007TE-07 | Abdominal - Medium Adult | 25.0 cm | 32.5 cm | 15.0 cm |
| 007TE-08 | Abdominal - Large Adult | 31.0 cm | 38.9 cm | 15.0 cm |

FIG. 12

| Patient Size (cm) | RMS Error (%) |
|---|---|
| 36.12 | 11.3 |
| 29.58 | 11.02 |
| 26.77 | 10.85 |
| 18.77 | 5.63 |
| 16.30 | 7.38 |
| 13.08 | 10.71 |
| 9.95 | 10.14 |

FIG. 13

| Patient Size (cm) | Dose (mGy) @ MDC = 0.5% for 7mm | Dose (mGy) @ MDC = 0.5% for 5mm |
|---|---|---|
| 36.12 | 39.8 | 69.1 |
| 29.58 | 20.3 | 37.4 |
| 26.77 | 14.2 | 26.8 |
| 18.77 | 4.2 | 8.4 |
| 16.30 | 2.7 | 5.5 |
| 13.08 | 1.5 | 3.1 |
| 9.95 | 0.8 | 1.7 |

MDC and measured contrast (MC) for 7mm and 5mm targets are tabulated.

FIG. 22

| Patient Size (cm) | Error (%) |
|---|---|
| 36.12 | 10.7 |
| 29.58 | 3.61 |
| 26.77 | 4.63 |
| 18.77 | 8.46 |
| 16.30 | 10.9 |
| 13.08 | 8.11 |
| 9.95 | 12.56 |

FIG. 23

| Patient Size (cm) | Dose (mGy) @ MDC = 0.5% for 7mm target | Dose (mGy) @ MDC = 0.5% for 5mm target |
|---|---|---|
| 36.12 | 27.6 | 50.2 |
| 29.58 | 11.2 | 23.7 |
| 26.77 | 10.1 | 21.5 |
| 18.77 | 2.2 | 4.7 |
| 16.30 | 1.1 | 2.4 |
| 13.08 | 0.6 | 1.3 |
| 9.95 | 0.7 | 1.3 |

FIG. 31

Table 1. Dose measurement results

| Scanner | Weighted Dose per 100mAs (mGy) | Center Dose/Periphery Dose |
|---|---|---|
| Scanner A | 8.00 | 0.54 |
| Scanner B | 8.35 | 0.50 |

FIG. 36

Table 2. Fitting parameters using the power law model in equation (8)

| Scanner | A | B | C | Correlation coefficient ($R^2$) |
|---|---|---|---|---|
| Scanner A | 18.046 | -1.027 | -0.537 | 0.993 |
| Scanner B | 14.054 | -1.116 | -0.492 | 0.999 |

FIG. 38

Table 3. Fitting parameters using the power law model in equation (11)

| Scanner | G | K | M | Correlation coefficient ($R^2$) |
|---|---|---|---|---|
| Scanner A | 0.292 | -1.030 | 1.015 | 0.994 |
| Scanner B | 0.270 | -1.119 | 1.004 | 0.999 |

SYSTEMS AND METHODS FOR DETERMINING RADIATION DOSE IN COMPUTED TOMOGRAPHY SCANS

CROSS-REFERENCE TO RELATED APPLICATIONS

This application is a National Phase of International Application No. PCT/US2014/049647, filed Aug. 4, 2014, currently pending, which designated the U.S. and that International Application was published under PCT Article 21(2) in English, which claims priority under 35 U.S.C. §119(e) to U.S. Provisional Application No. 61/862,415, filed Aug. 5, 2013, and U.S. Provisional Application No. 62/026,459, filed Jul. 18, 2014, the contents of all of which are hereby incorporated herein by reference in their entirety.

FIELD OF THE INVENTION

The present invention relates generally to imaging systems and methods for computed tomography (CT), and more particularly, to determining a radiation dose for imaging with a CT scanner.

BACKGROUND

The following description includes information that may be useful in understanding the present disclosure. It is not an admission that any of the information provided herein is prior art or relevant to the presently claimed invention.

A study that tracked pediatric CT radiation doses in large health maintenance organizations across the U.S. found that the volume of CT scans nearly doubled between 1996 and 2005, and that the scans put young patients at greater risk of future cancer. While CT imaging is beneficial for diagnosing and monitoring the progression of a patient's condition, there is a need in the art for improved systems and methods for reducing the radiation exposure of a patient.

SUMMARY OF THE INVENTION

According to one aspect of the present disclosure, a computed tomography (CT) imaging system for imaging a body region of a subject comprises CT scanner circuitry including one or more processing units and one or more memory devices. The one or more memory devices store instructions that, when executed by at least one of the one or more processing units, cause the CT scanner circuitry to implement the acts of receiving first input data indicative of a lesion size of interest, receiving second input data indicative of a predetermined minimum detectable contrast (MDC), receiving third input data associated with a size of a subject being imaged, determining a value for the size of the subject based on the received third input data, and determining a radiation dose to apply to the subject. The determining of the radiation dose is based on a power law model relating size of the subject, lesion size, and minimum detectable contrast. The power law model is defined as $MDC = A(L) d^{B(L)} Dose^{C(L)}$, wherein (i) MDC is the predetermined minimum detectable contrast, (ii) d is the lesion size, (iii) Dose is radiation dose, (iv) A(L), B(L), and C(L) are pre-determined fitted parameters for the CT imaging system, and (v) L is the determined value for the size of the subject. A radiation source is configured to rotate about the body region of the subject and emit the determined radiation dose. A radiation detector senses radiation doses emitted from the radiation source. The detector generates electronic signals in response to the sensed radiation doses. The electronic signals represent image data received by the CT scanner circuitry and used to generate an image of at least a portion of the body region of the subject.

According to another aspect of the present disclosure, a method determines a minimum radiation dose for a computed tomography (CT) scanning device that includes CT scanner circuitry including one or more processing units. The method comprises the acts of receiving in the CT scanner circuitry a first input indicative of a selected minimum detectable contrast. A second input indicative of an estimate of a size of a subject to be exposed to the radiation dose is received in the CT scanner circuitry. A minimum radiation dose to be applied via a radiation source of the CT scanning device is determined via at least one of the one of more processing units. The minimum radiation dose is determined at least in part by a power law model relating the size of the subject, a lesion size, and a minimum detectable contrast. The power law model is defined as $MDC = A(L) d^{B(L)} Dose^{C(L)}$, wherein (i) MDC is the selected minimum detectable contrast, (ii) d is lesion size, (iii) Dose is radiation dose, (iv) A(L), B(L), and C(L) are pre-determined fitted parameters for the CT imaging system, and (v) L is the estimate of the size of the subject.

According to yet another aspect of the present disclosure, a method determines a radiation dose for a computed tomography (CT) scanning device that includes CT scanner circuitry including one or more processing units. The method comprises the acts of receiving in the CT scanner circuitry a first input of scout view image data. A subject size is determined from the received scout view image data via at least one of the one or more processing units. A plurality of radiolucent dosimeters are placed on an exterior surface of the subject. A dose of radiation is applied to the subject via a radiation source of the CT scanning device. A peripheral radiation dose, $Dose_p$, is determined based upon the exposure of at least one of the plurality of dosimeters to the applied dose of radiation via at least one of the one or more processing units. A patient specific weighted dose and/or center dose to which a subject has been exposed is determined, via at least one of the one or more processing units, according to the relationships defined by the following equations $$Dose_c = \frac{2r}{3-r} Dose_p \text{ and } Dose_w = \frac{2}{3-r} Dose_p,$$

wherein $Dose_c$ is the center dose, $Dose_w$ is the weighted dose, and $$r = \frac{Dose_c}{Dose_w},$$

and wherein a value for r is obtained for different subject sizes from a predetermined Gaussian relationship between r and equivalent subject diameters.

Additional aspects of the present disclosure will be apparent to those of ordinary skill in the art in view of the detailed description of various embodiments, which is made with reference to the drawings, a brief description of which is provided below.

BRIEF DESCRIPTION OF THE DRAWINGS

Features and advantages of the present disclosure will become more apparent from the following detailed description of exemplary embodiments thereof taken in conjunction with the accompanying drawings in which:

FIG. 4 illustrates specifications for exemplary phantoms in accordance with aspects of the present disclosure.

FIG. 12 demonstrates a listing of errors determined using a power law model on minimum detectable contrast (MDC) for a Siemens Sensation 64 CT machine, in accordance with aspects of the present disclosure.

FIG. 13 demonstrates exemplary dose computations using a Siemens Sensation 64 CT machine, in accordance with aspects of the present disclosure.

FIG. 22 demonstrates a listing of errors determined using a power law model on minimum detectable contrast (MDC) for a GE HD750 CT machine, in accordance with aspects of the present disclosure.

FIG. 23 demonstrates exemplary dose computation examples using a GE HD750 CT machine, in accordance with aspects of the present disclosure.

FIG. 31 lists exemplary dose measurement results, in accordance with aspects of the present disclosure.

FIG. 36 lists exemplary fitting parameters based on the power law in equation (8), in accordance with aspects of the present disclosure.

FIG. 38 lists exemplary fitting parameters based on the power law in equation (11), in accordance with aspects of the present disclosure.

Figure 1:
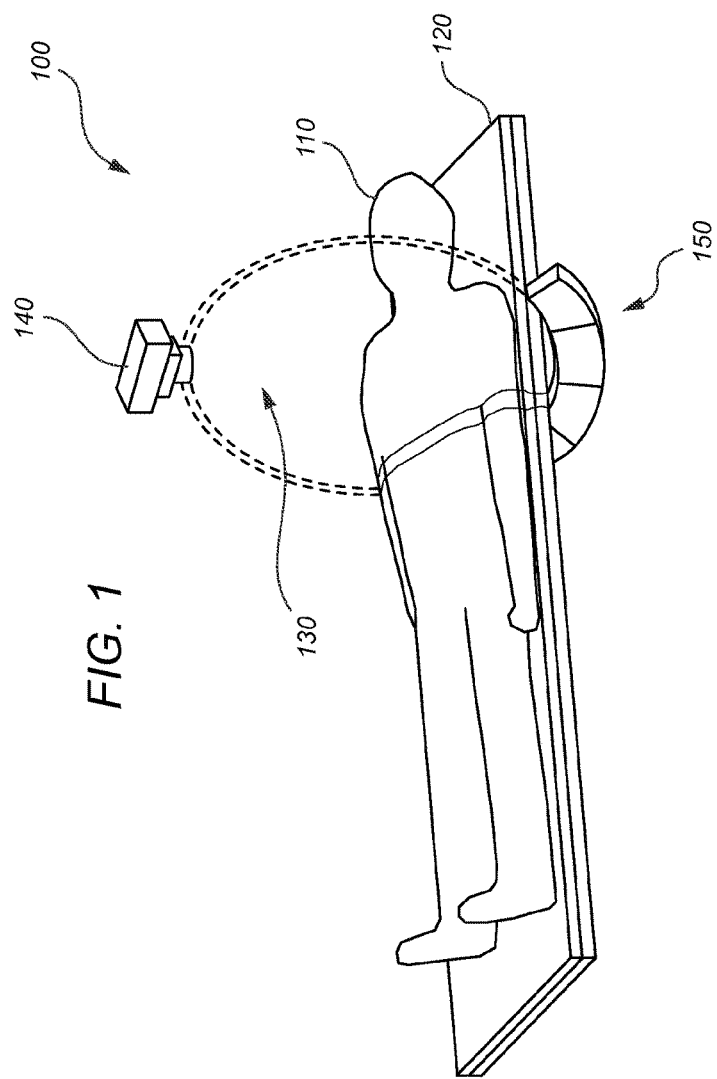
FIGS. 1 and 2 illustrate exemplary aspects of a computed tomography imaging system.

While the present disclosure is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred aspects of the invention with the understanding that the present disclosure is to be considered as an exemplification of the principles of the invention and is not intended to limit the broad aspect of the invention to the aspects illustrated.

Unless defined otherwise, technical and scientific terms used herein have the same meaning as commonly understood by one of ordinary skill in the art to which this invention belongs. Webb et al. *Fundamentals of Body CT* (2006); and Guyton and Hall, *Textbook of Medical Physiology* 12$^{th}$ ed., provide one skilled in the art with a general guide to many of the terms used in the present application.

For purposes of the present disclosure, certain terms are defined as follows. As used herein, the acronym "CT" means computed tomography. As used herein, the acronym "AEC" means automatic exposure control. As used herein, the acronym "LCD" means low contrast detectability. As used herein, the acronym "MDC" means minimum detectable contrast. As used herein, the acronym "FBP" means filtered backprojection. As used herein, the acronym "SF-LCD" means statistically defined low contrast detectability. As used herein, "mammal" refers to any member of the class Mammalia, including, without limitation, humans and non-human primates such as chimpanzees and other apes and monkey species; farm animals, such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

Computed tomography (CT) is a noninvasive procedure that uses X-ray equipment in the form of a CT scanner to produce cross-sectional images of the body of a subject being examined. The series of cross-sectional images represent "slices" of the subject. These cross-sectional images can be used for a variety of diagnostic and therapeutic purposes.

Figure 2:
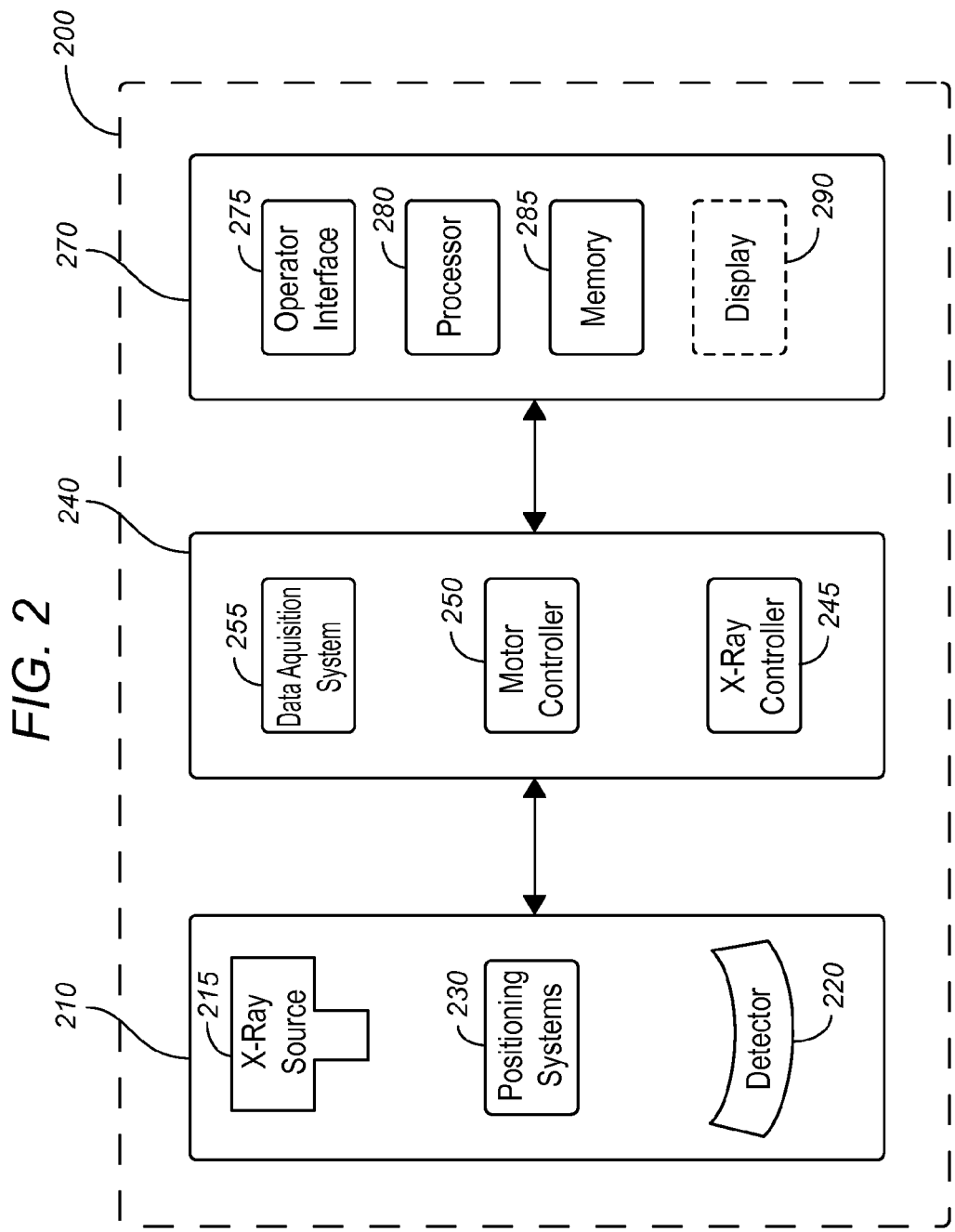

Turning now to FIGS. 1 and 2, exemplary aspects of CT imaging systems 100, 200 are illustrated. A subject 110 (e.g., a patient) may be positioned on a table 120 that is configured, via a motorized system, to move the table to multiple positions through a circular opening 130 in the CT imaging system 100. An X-ray source 140 (or other radiation source) and detector element(s) 150 are a part of the CT imaging system and are configured to rotate around the subject 110 while the subject is inside the opening 130. In a typical CT device, a single rotation takes approximately one second or less. During the rotation of the X-ray source and/or detector, the X-ray source produces a narrow, fan-shaped (or cone-shaped) beam of X-rays that pass through a targeted section of the body of the subject being imaged. The detector element(s) (e.g., multi-ring detector elements) are opposite the X-ray source and register the X-rays that pass through the body of the subject being imaged and in that process record a snapshot used to create an imager. Many different snapshots at many angles through the subject are collected through one rotation of the X-ray source and/or detector element(s). The image data generated by these collected snapshots are transmitted to a computer that reconstructs the image data based on the snapshots into one or several cross-sectional images of interior of the body (e.g., internal organs or tissues) of the subject being scanned by the CT device.

Referring now to FIG. 2, an exemplary CT imaging system 200 is illustrated that includes an imaging source-detector module 210, a controller-acquisition module 240, and a processor-interface module 270, where all three components are in operative communication with each other and may be part of one device or may be separated into their individual components or any combinations thereof. The imaging source-detector module 210 includes an X-ray source 215 that projects a beam of X-rays toward a detector array 220 located on an opposite side of a donut-shaped support structure (not shown), similar to the system illustrated in FIG. 1. The imaging source-detector module 210 can further include a positioning system 230 that positions an area of interest (e.g., specific organs of interest), for a subject (e.g., a mammal) being imaged, between the X-ray source 215 and the detector array 220. The detector array 220 can include one or more detector elements that receive and sense the projected X-rays that pass through the area of interest of the subject being imaged. The detector element(s) of the detector array produce electrical signal(s) that represent the intensity of the sensed X-ray beam, which is attenuated to varying degrees as it passes through, for example, the different tissues of the mammal being imaged.

The controller-acquisition module 240 can include an X-ray controller 245, a motor controller 250, and a data acquisition system 255. For example, the X-ray controller can provide the power and timing of signals to the X-ray source 215. The motor controller can be configured to control the positioning system 230, which might include the positioning of a table supporting the subject and/or the positioning of the X-ray source 215 and detector array 220 about the subject. The data acquisition system 255 can be used to collect data from the detector array 220, where the data is subsequently processed to produce the desired cross-sectional image of the area of interest in the subject.

The processor-interface module 270 can include one or more of the following elements such as an operator interface 275, one or more processing units 280, one or more memory devices 285, and/or one or more display devices 290. The process-interface module 200 is configured to both send and receive information from the controller-acquisition module 240. For example, the processor-interface component may receive commands and CT scanning parameters through the operator interface 275. The operator may be able to observe the CT image that is reconstructed from the imaging data along with other data on the display device 290. Furthermore, the operator supplied commands and scanning parameters can be used to provide control signals and other information to the controller-acquisition module 240 including to the X-ray controller 245 and the motor controller 250. Image data and controller feedback can also be received and processed by the processor-interface module 270.

In earlier imaging systems prior to CT scanners, such as with conventional plain film examinations, radiation dose was adjusted depending on patient size to avoid overexposing or underexposing the film. One of the benefits of CT scanning technology was that film exposure problems were eliminated, which led to doses being gradually increased because higher doses meant a less grainy image and better image resolution. As the use of CT scanners increased, concerns about radiation exposure grew, such as for pediatric patients.

CT is a modality of choice for many diagnostic tasks due to its ease of use and the growing clinical applications. However, it is desirable to minimize exposure to radiation dose. Currently, there exists a wide variation of protocols for the same application, which has led to unnecessary radiation exposure for living beings being evaluated using CT, which can be a particular concern, for example, for pediatric patients.

It is contemplated that optimizing radiation dosages with the objective of consistent image quality reduces the unnecessary exposure to radiation. However, in the realm of low contrast lesion diagnosis, simplified image quality metric such as pixel noise (pixel standard deviation) or contrast-to-noise ratio (CNR) are not necessarily appropriate because neither adequately delineates the low contrast details well. It would be desirable for radiation dosing to be determined by the required detectability of the lesion. This can be particularly beneficial in abdominal CT studies where the detection of low contrast lesions is desirable along with minimizing radiation dose is desirable, as well.

While radiation dose is generally understood to be adjusted for patient size, a system and method that minimizes discrepancies in the dose adaptation would be beneficial that accounts for quantitative relationships between contrast detectability and dose, lesion size, and the size of the subject being imaged. These beneficial systems and methods can be based on machine specific relationships determined using parametric models. The parametric models can further be validated by conducting experiments on realistically shaped tissue equivalent abdomen phantoms representative of infant to large patients, such as in the case of human subjects. It would also be desirable to identify a detectability to pixel noise relationship, which may, for example, be directly obtained from CT's AEC. By applying the parametric models, a technical solution can be obtained to the problem of determining radiation doses for CT scanners. The parametric models allow for determining and applying the radiation dose needed to detect a lesion of certain size and contrast for a known subject size.

In some embodiments, the present disclosure describes a method for determining a radiation dose to administer to a subject during a CT scan by (a) specifying a desired contrast for a lesion size of interest in the subject; (b) determining the size of the subject; and (c) determining a radiation dose to administer to the subject during the CT scan by using a power law that relates subject's size, lesion size, and minimum detectable contrast according to the relationship defined by $MDC = A(L) d^{B(L)} Dose^{C(L)}$, wherein (1) MDC is minimum detectable contrast, typically expressed as a percentage, (2) d is lesion (or target) size, sometimes expressed in millimeters, (3) Dose is radiation dose, often expressed in milligrays (mGy), (4) A(L), B(L), and C(L) are fitted parameters particular to a specific CT machine, and (5) L is the subject's size, often expressed in centimeters.

Figure 24:
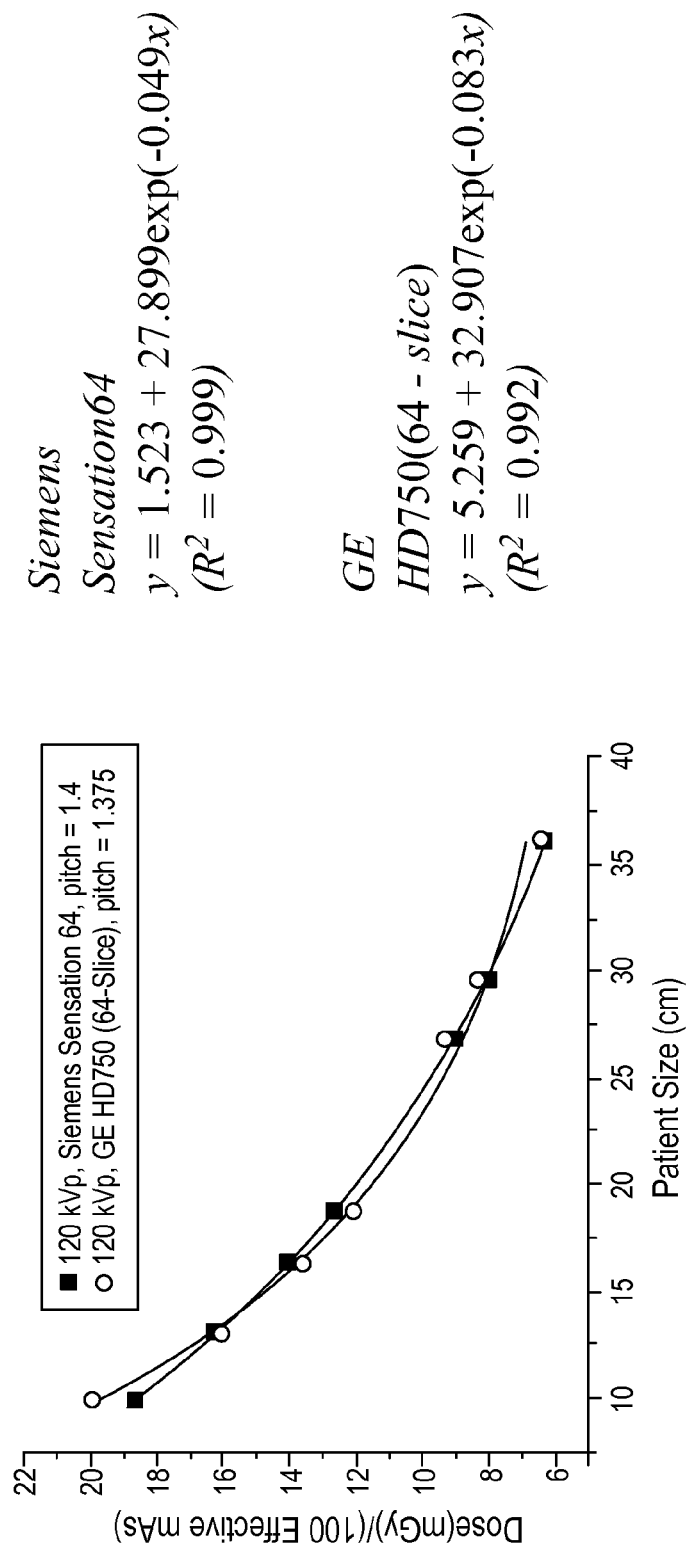
FIG. 24 illustrates a graph including exemplary dose to techniques lookup curves for a Siemens Sensation 64 CT machine and a GE HD750 CT machine, in accordance with aspects of the present disclosure.
Figure 25:
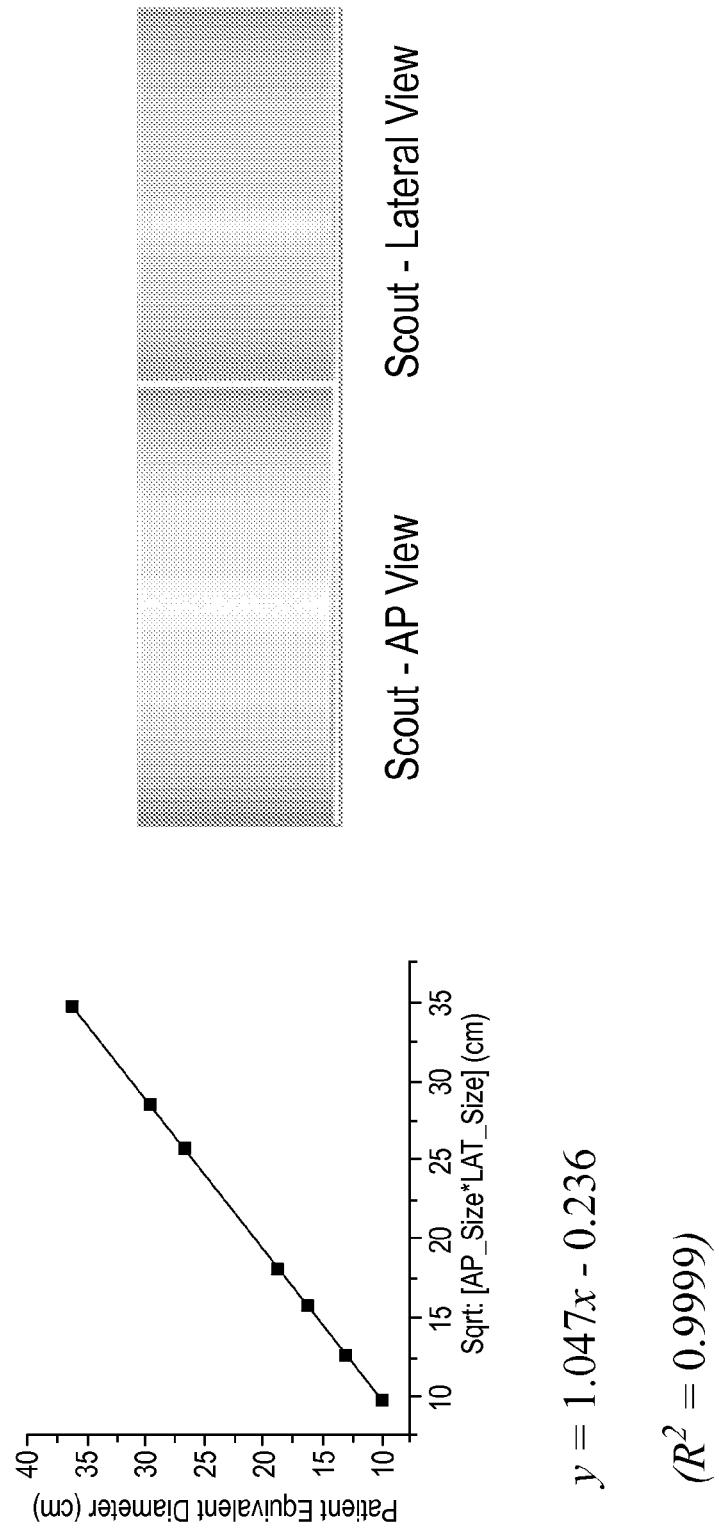
FIG. 25 illustrates an exemplary determination of patient size using 2-view scout phantom results including AP (left) and lateral (right) scout views, in accordance with aspects of the present disclosure.

In certain embodiments, fitted parameters are determined by analyzing data obtained by scanning phantoms representative of a range of subject sizes, using a CT machine of the type that will be used to perform the CT scan on the subject. In some embodiments, the inventive method includes using a previously determined lookup curve (as shown in FIG. 24) to determine an appropriate acquisition technique. In various embodiments, two-view (AP and lateral) scout images are acquired and subsequently used to estimate the subject's size (as shown in FIG. 25), which is then used to determine the appropriate dose according to aspects described in the present disclosure.

In certain embodiments, a system for administering a CT scan to a subject is described that includes (1) estimating the subject's size (as indicated above); (2) obtaining the appropriate dose from a user programmed minimum detectable contrast (MDC) requirement on the console of a CT machine; (3) converting the dose to beam current (in milli-Ampere) and rotation time product (in sec.) under a certain kVp using a previously determined look-up-table; and (4) scanning the subject with the CT machine.

In certain embodiments, the invention teaches converting MDC to noise according to the relationship $$MDC\% = \frac{0.300 N_p}{d}$$

or $MDC\% = 0.253 N_p/d$, for a Siemens Sensation 64 CT scanner and a GE Discovery HD750 CT scanner, respectively, wherein $N_p$ is pixel noise and d is lesion size. In some embodiments, AEC implementation can then be adjusted.

In certain embodiments, a program or instructions are embodied on a non-transitory computer readable medium for calculating an appropriate radiation dose for a subject, said program configured to use relationships defined by a power law for calculating a radiation dose, when contrast, lesion size of interest and subject size are provided. In some embodiments, the power law relates subject size, lesion size, and minimum detectable contrast according to $MDC = A(L) d^{B(L)} Dose^{C(L)}$, wherein MDC is minimum detectable contrast, d is target size, Dose is radiation dose, A(L), B(L), and C(L) are fitted parameters particular to a specific CT machine, and L is subject size.

In some embodiments, a method is described for determining a dose of radiation from the surface dose to which a subject has been exposed, including: acquiring two or more scout view images to determine the subject's size; placing two or more radiolucent dosimeters on the surface of the subject; using a CT machine to apply a dose of radiation to the subject; determining a peripheral dose based upon dosimeter exposure; and determining the subject specific weighted dose and/or center dose to which the subject has been exposed according to the relationships defined by the following equations:

$$Dose_c = \frac{2r}{3-r} Dose_p \text{ and } Dose_w = \frac{2}{3-r} Dose_p,$$

wherein $Dose_c$ is the center dose, $Dose_w$ is the weighted dose, $Dose_p$ is the peripheral dose, and $$r = \frac{Dose_c}{Dose_w}.$$

Figure 26:
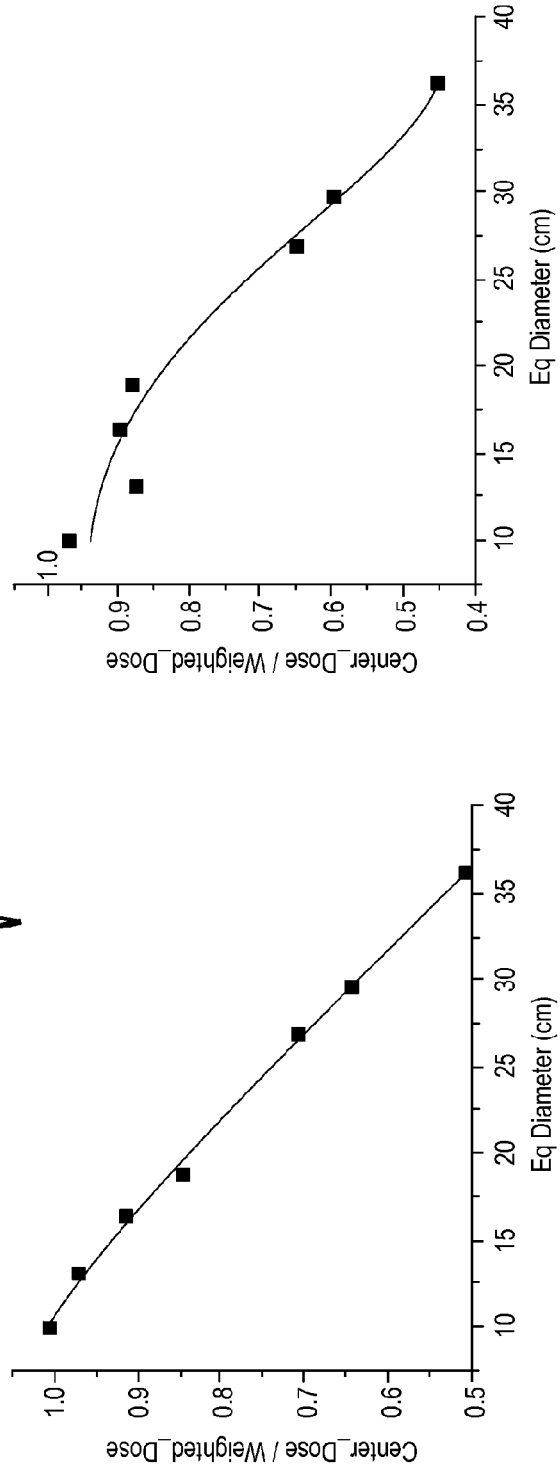
FIG. 26 illustrates graphs with results showing center dose/weighted dose vs. patient size for the Siemens Sensation 64 (left) and GE HD750 (right), in accordance with aspects of the present disclosure.

The ratio r for different patient sizes can be obtained from FIG. 26 (Gaussian relationships). In certain embodiments, the radiolucent dosimeters are calibrated using ion chambers in phantoms.

In some aspects of the systems and methods described in the present disclosure, fitted parameters are determined for a parametric model that determines a minimum radiation dose for providing a minimum detectable contrast. The fitted parameters are determined by analyzing data obtained by scanning phantoms representative of a range of lesion sizes and radiation doses using a CT machine of the same or similar type that may be used to perform a CT scan on an actual subject or patient.

It is contemplated that a CT scanner system or a CT machine according to some aspects of the present disclosure includes one or more input devices, one or more display devices, and CT scanner circuitry. The CT scanner circuitry can include one or more central processing units and one or more memory devices (e.g., that may be included in any one of the imaging source-detector, controller-acquisition, and/or processor-interface modules 210, 240, 270). The one or more memory devices store instructions that, when executed by the one or more central processing units, cause the CT scanner circuitry to implement the acts in one or more of the method acts described in the present disclosure. In some aspects, CT images are displayed on the one or more display devices. In some aspects, inputs are received by at least one of the one or more input devices. In some aspects, the CT scanner system or the CT machine further includes a transmitter for generating a beam current and rotation time product at the determined minimum radiation dose, and a receiver for generating CT image signal data in response to radiation generated by the beam current and reflected from the subject.

It is contemplated that in some aspects of the present disclosure, a computer program is embodied on a non-transitory computer readable medium for calculating a radiation dose for a subject. The program includes instructions operative to implement the acts of any one of methods acts described herein when the instructions are executed on a physical processing unit.

In some aspects of the present disclosure, the CT machines used in conjunction with the described systems and/or methods can include, but are in no way limited to, modified versions of commercially available system such as the Siemens Biograph 64, Siemens Sensation 64, GE HD750, GE VCT, Toshiba 64 and Philips 64-slice CT scanners, and the like, as such products are available from the General Electric Company of Fairfield, Conn., USA (and its GE Healthcare subsidiary), Siemens AG of Erlangen, Germany (and its Siemens Medical Solutions USA, Inc. subsidiary, of Malvern, Pa., USA), and Koninklijke Philips N.V. of Amsterdam, Netherlands (and its Philip Healthcare subsidiary, of Andover, Mass.).

In some embodiments, the systems and methods described herein are applied to mammals. In some embodiments, the inventive systems and methods described herein are applied to humans. In various embodiments, the CT scans performed according to the inventive methods are CT scans of the abdomen. In some embodiments, the CT scans performed according to the inventive methods are CT scans of a child's abdomen. In some embodiments, the target is a lesion.

One skilled in the art will recognize many methods, systems, and/or materials similar or equivalent to those described herein, which could be used in the practice of the present invention. Indeed, the present invention is in no way limited to the methods, materials, and/or system described herein.

Referring now to FIGS. 3-26, various experimental procedures, analyses, and results are described related to determining patient- or subject-size dependent radiation dosing for obtaining consistent low contrast detectability in CT.

In view of risks associated with radiation exposure, a reasonable dose for CT for medical imaging purposes can be described as a minimum possible dose that achieves a predetermined imaging quality. With a goal of establishing a method for determining and delivering such a patient- or subject-specific dose, a power law model has been developed based upon the relationship between select variables, as defined by:

$$MDC = A(L) d^{B(L)} Dose^{C(L)} \qquad (1)$$

where MDC is minimum detectable contrast, d is target size, Dose is radiation dose, $A(L)$, $B(L)$, and $C(L)$ are fitted parameters particular to a specific CT machine, and L is patient size.

Figure 3:
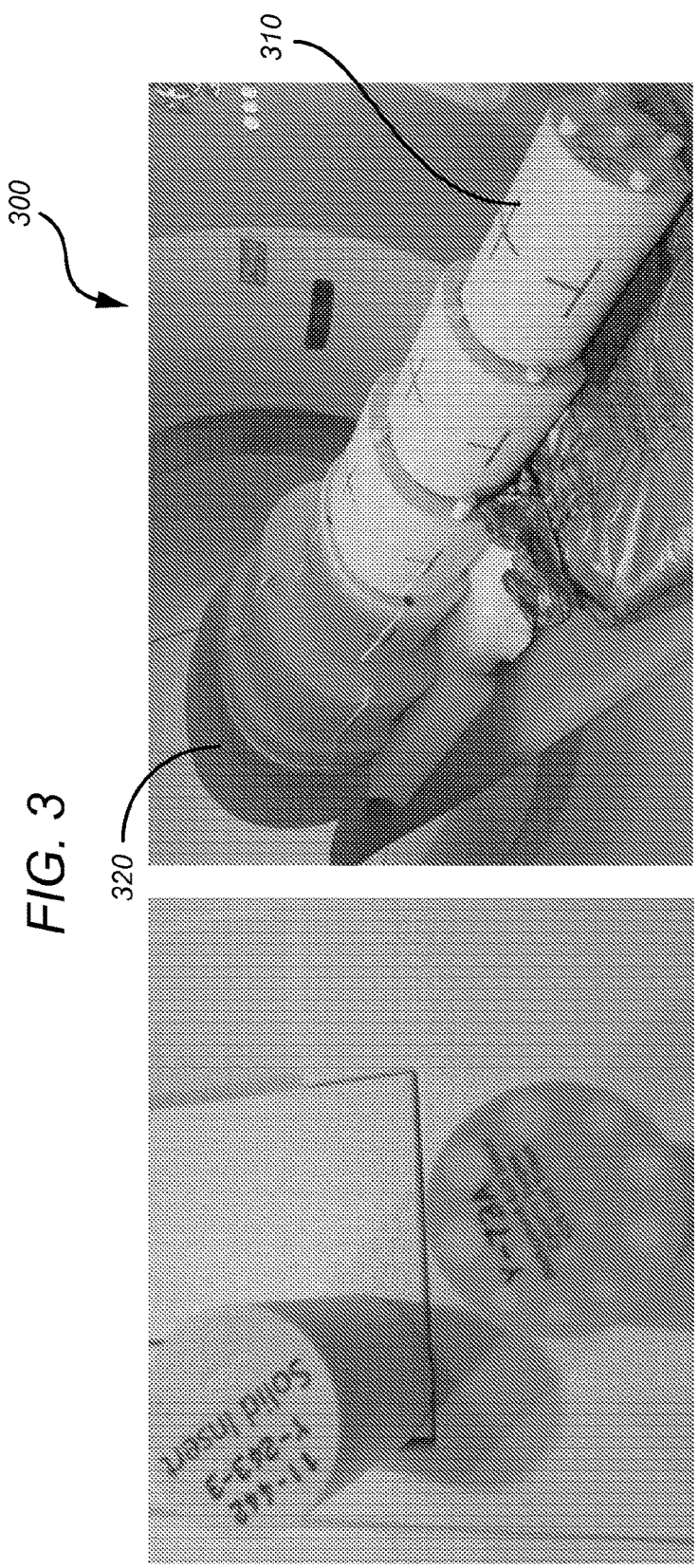
FIG. 3 illustrates exemplary CT abdomen phantoms, in accordance with aspects of the present disclosure.
Figure 5:
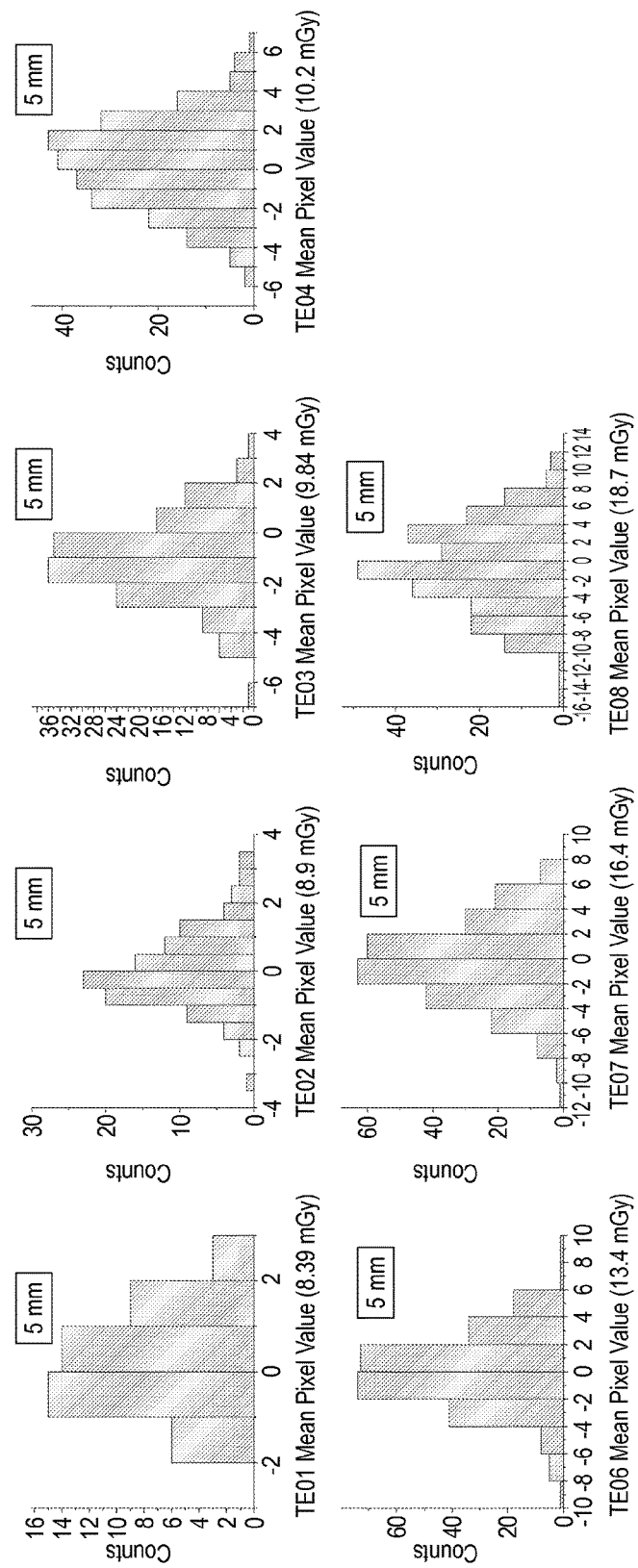
FIG. 5 illustrates normal distributions as determined by the Kolmogorov-Smirnov test in accordance with aspects of the present disclosure.
Figure 6:
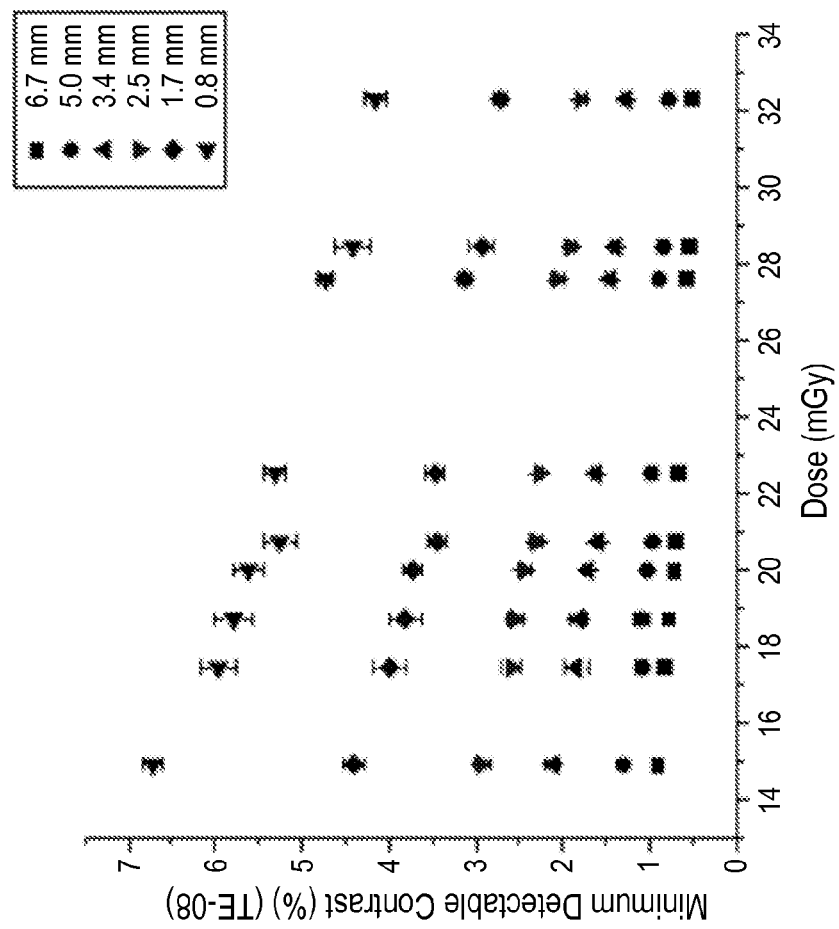
FIG. 6 illustrates a graph with results from scanning a phantom TE08 with a Siemens Sensation 64 CT machine, in accordance with aspects of the present disclosure.
Figure 7:
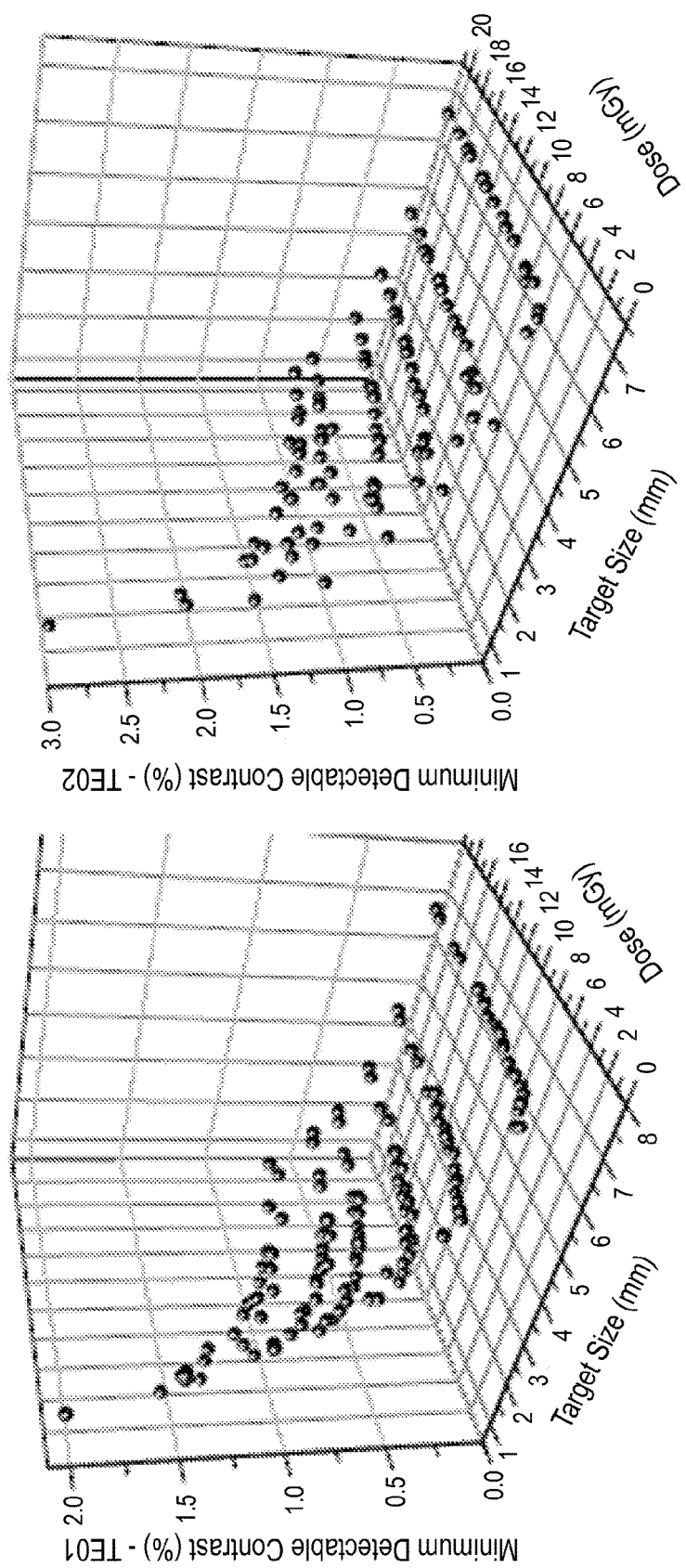
FIG. 7 illustrates graphs with results from scanning phantoms TE01 (left) and TE02 (right) using a Siemens Sensation 64 CT machine, in accordance with aspects of the present disclosure.
Figure 8:
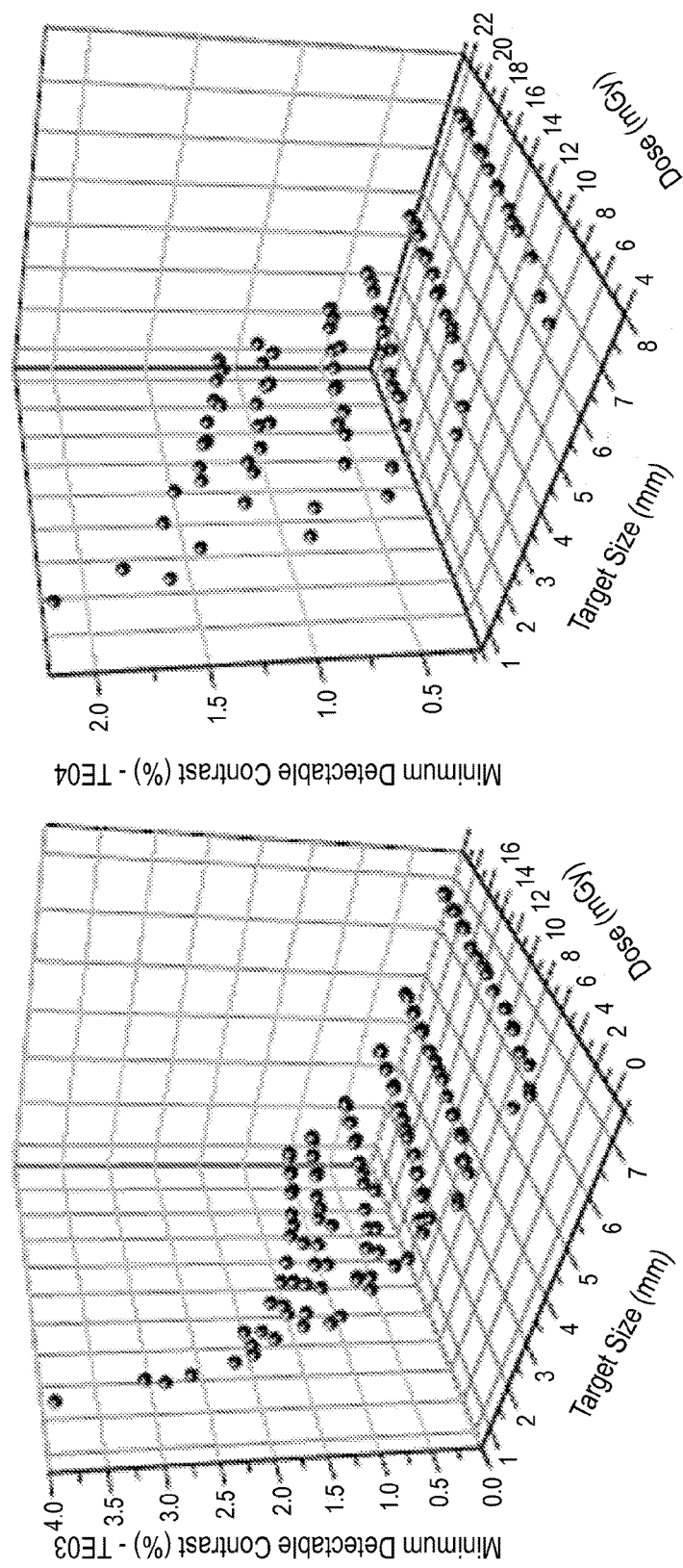
FIG. 8 illustrates graphs with results from scanning phantoms TE03 (left) and TE04 (right) using a Siemens Sensation 64 CT machine, in accordance with aspects of the present disclosure.
Figure 9:
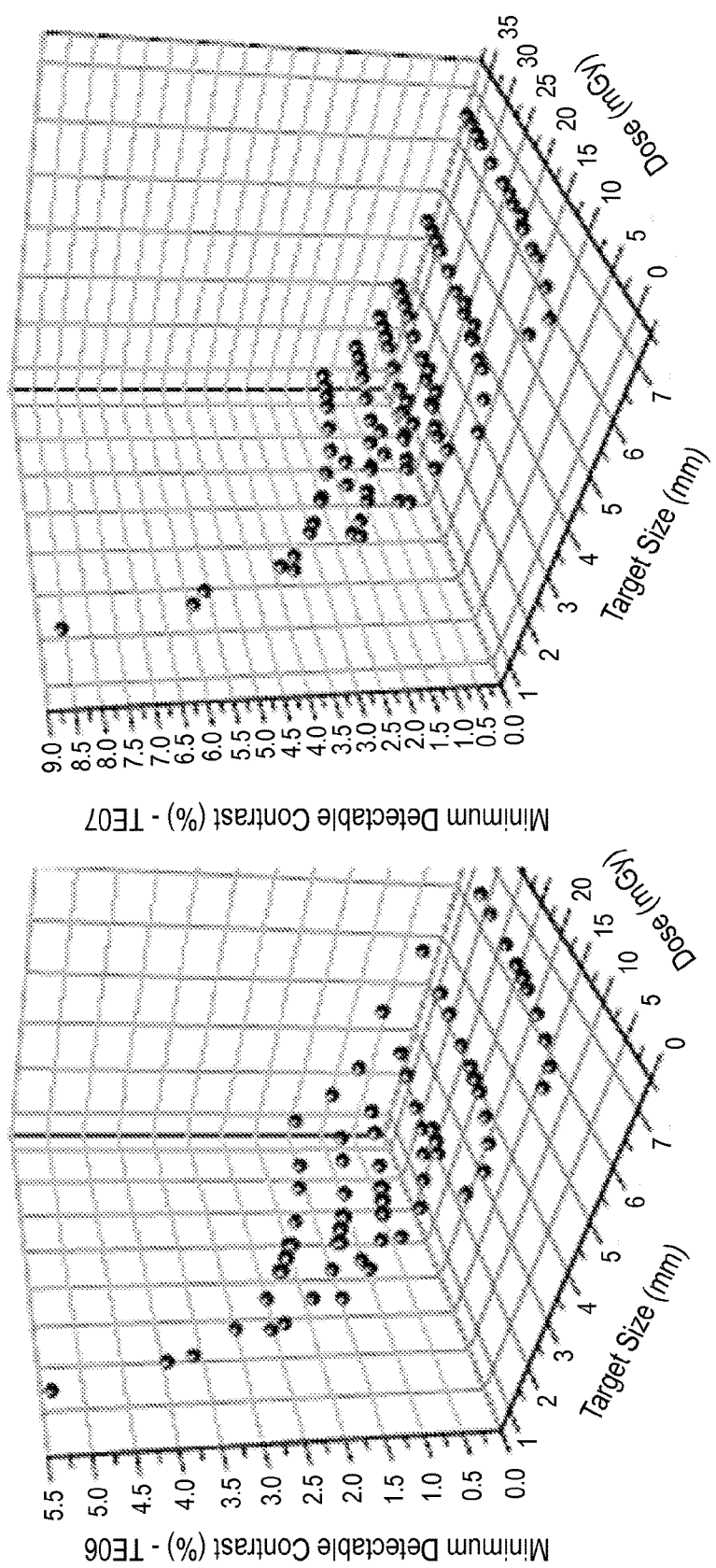
FIG. 9 illustrates graphs with results from scanning phantoms TE06 (left) and TE07 (right) using a Siemens Sensation 64 CT machine, in accordance with aspects of the present disclosure.
Figure 10:
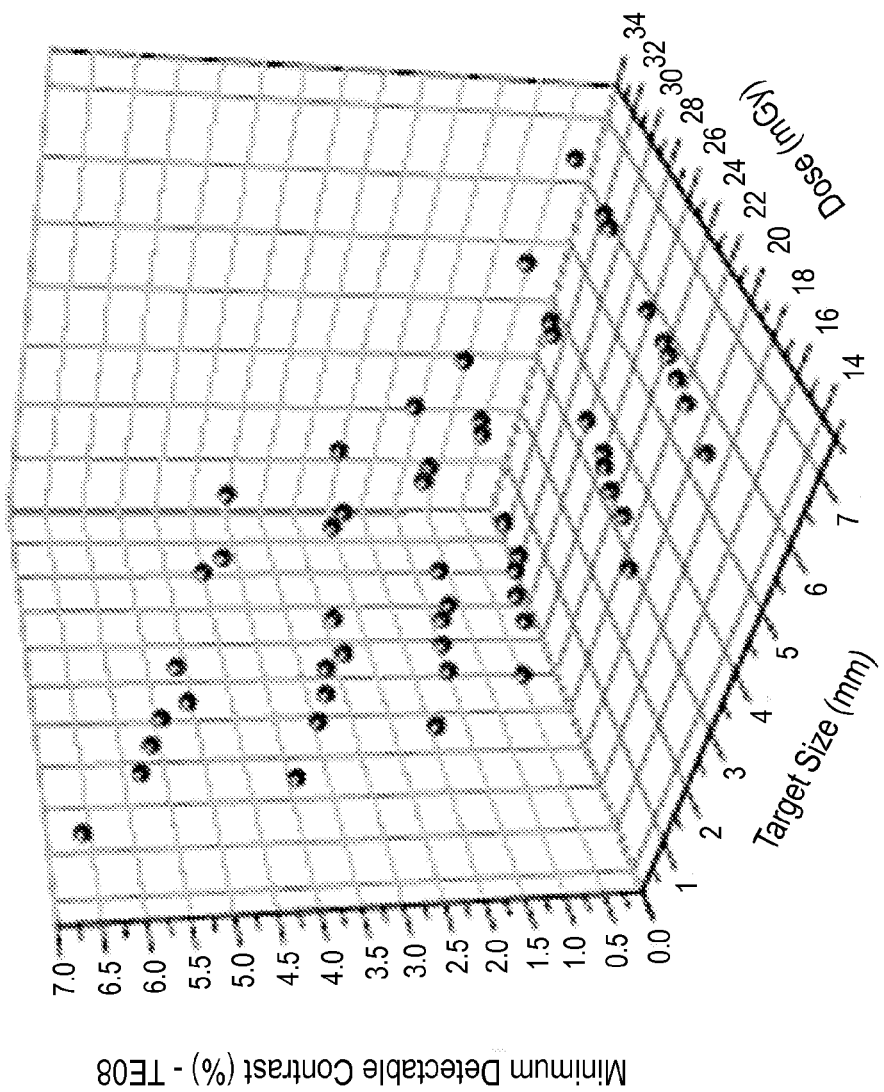
FIG. 10 illustrates a graph with results from scanning phantom TE08 using a Siemens Sensation 64 CT machine, in accordance with aspects of the present disclosure.

The power law model was evaluated experimentally using realistically shaped tissue equivalent abdomen phantoms, exemplary aspects of which are illustrated in FIG. 3, that simulate the human body. Infant to large patient sizes were used, and the specifications of the phantoms are described in FIG. 4. The CT scanners used for the experiments reported herein were Siemens Sensation 64S and GE HD750 (64S). For helical abdomen scans, the parameters used were 80-120 kVp, thickness=5 mm, pitch=1.4 Siemens, pitch=1.375 GE, Recon kernel B31—Siemens, and standard-GE. Subtraction of adjacent slices (8 center slices) was performed. Matrix element closest to 7, 5, 3.5, 2.5, 1.8, 1.2 mm. The exact matrix element size is determined by the integer number of pixels. The dose was measured on each phantom (size specific) instead of using standard 16-cm or 32-cm CTDI phantom. Normal distributions were determined for scans of the TE01-TE04 and TE06-TE08 phantoms using the Kolmogorov Smirnov Test, exemplary aspects of which are illustrated in the graphs presented in FIG. 5 for a 5-mm target for different sized abdominal phantoms.

Figure 11:
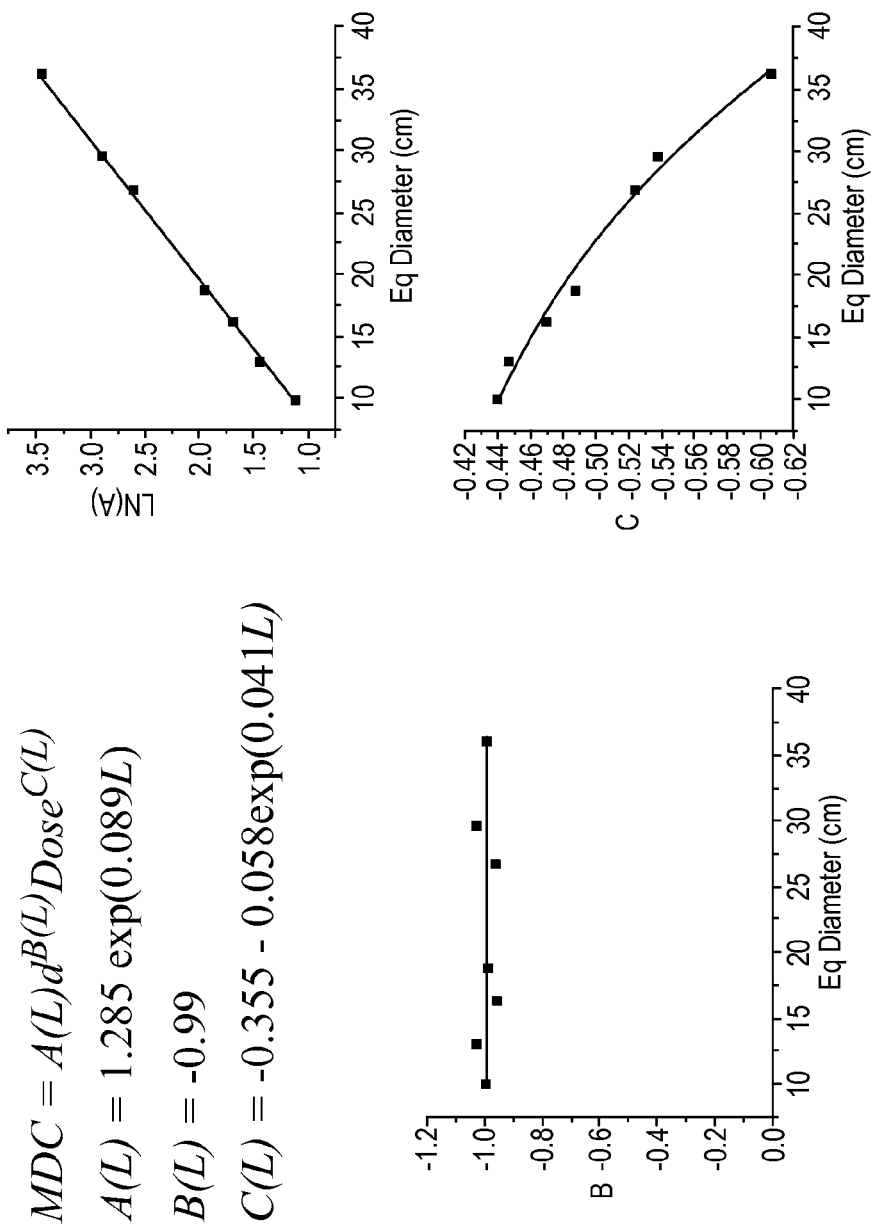
FIG. 11 illustrates a graph with exemplary fitting parameters versus patient size for a Siemens Sensation 64 CT machine, in accordance with aspects of the present disclosure.

Results of the scans performed on the Siemens Sensation 64 machine are shown in FIGS. 6-10. Fitted parameters specific to the Siemens Sensation 64 machine were then established, as shown in FIG. 11. Errors using the power law model on MDC for the Siemens Sensation 64 machine are shown in FIG. 12. Dose computation examples are shown in FIG. 13.

Figure 14:
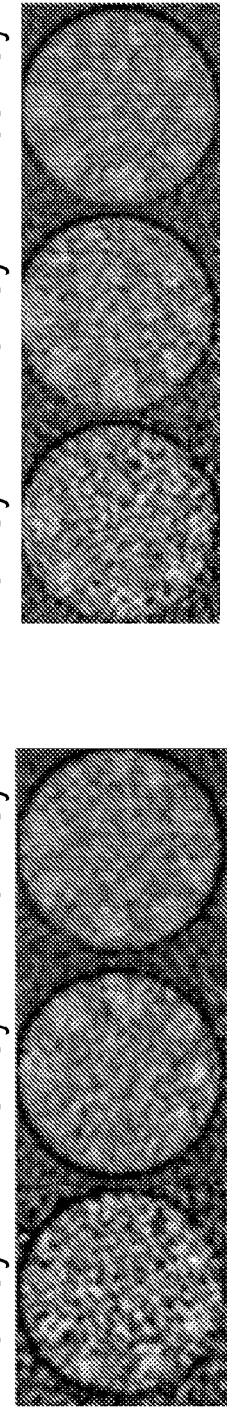
FIG. 14 illustrates MDC and measured contrast (MC) for exemplary 7 mm and 5 mm targets tabulated for Siemens Sensation 64 and GE HD750 CT machines, in accordance with aspects of the present disclosure.
Figure 15:
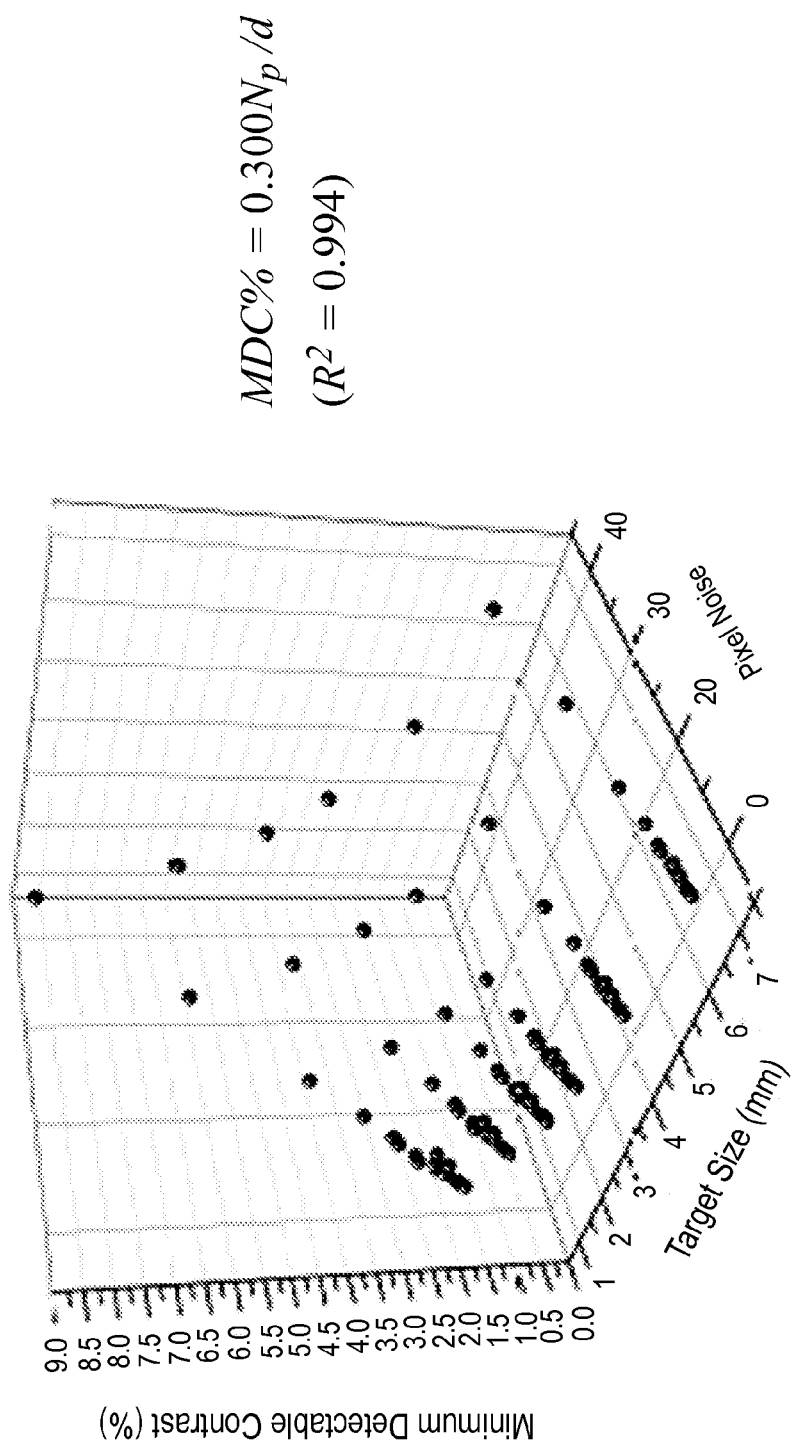
FIG. 15 illustrates a graph including correlations to pixel noise after scanning phantom TE07 (representing medium patient size) with a Siemens Sensation 64 CT machine, in accordance with aspects of the present disclosure.
Figure 16:
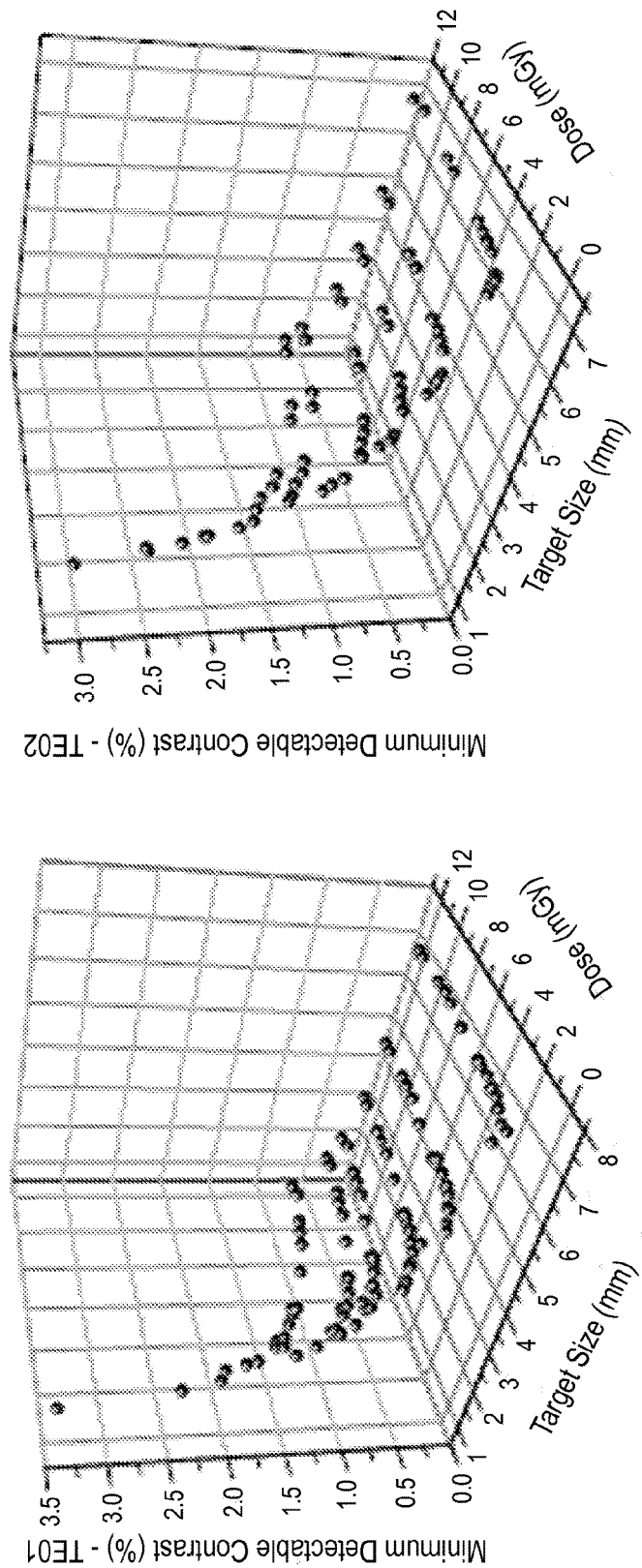
FIG. 16 illustrates graphs with results from scanning phantoms TE01 (left) and TE02 (right) using a GE HD750 CT machine, in accordance with aspects of the present disclosure.
Figure 17:
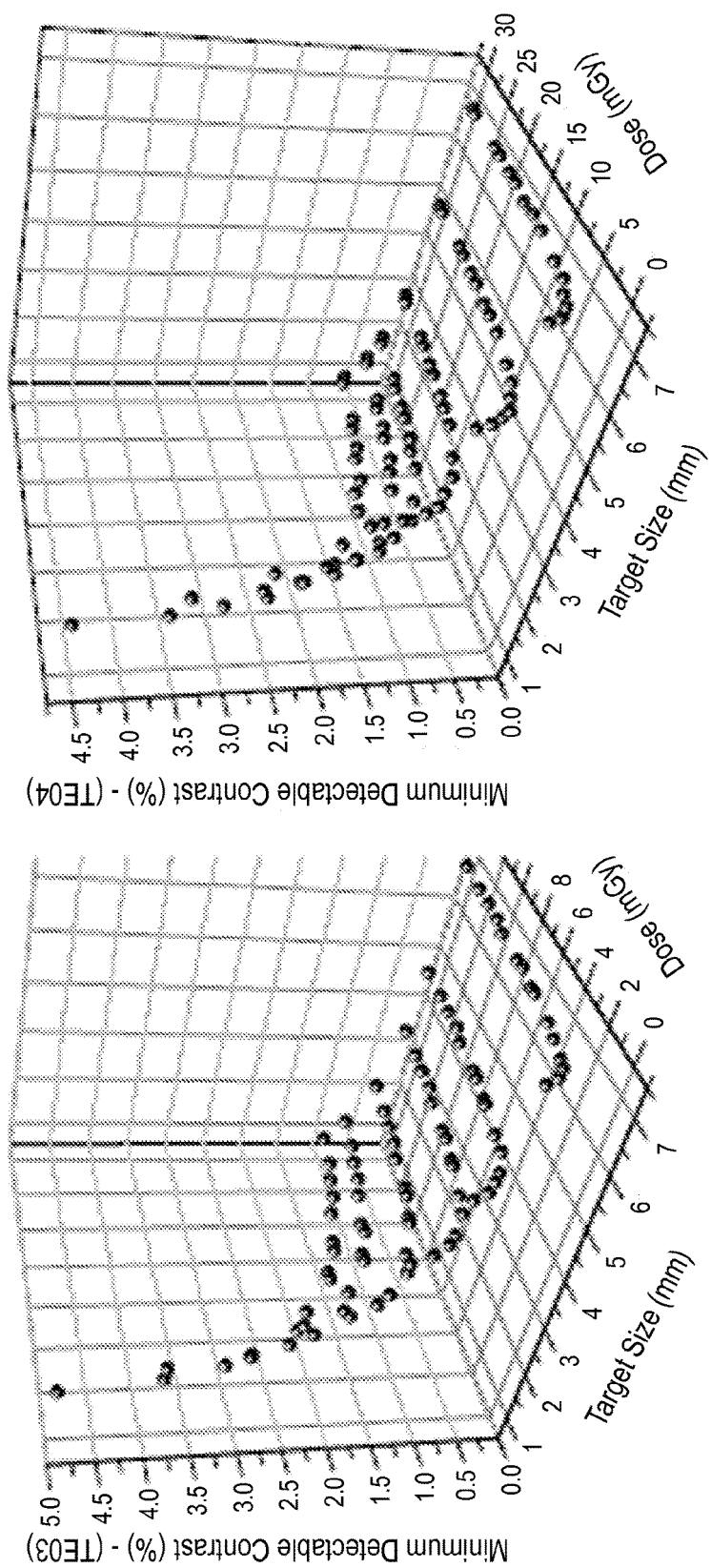
FIG. 17 illustrates graphs with results from scanning phantoms TE03 (left) and TE04 (right) using a GE HD750 CT machine, in accordance with aspects of the present disclosure.
Figure 18:
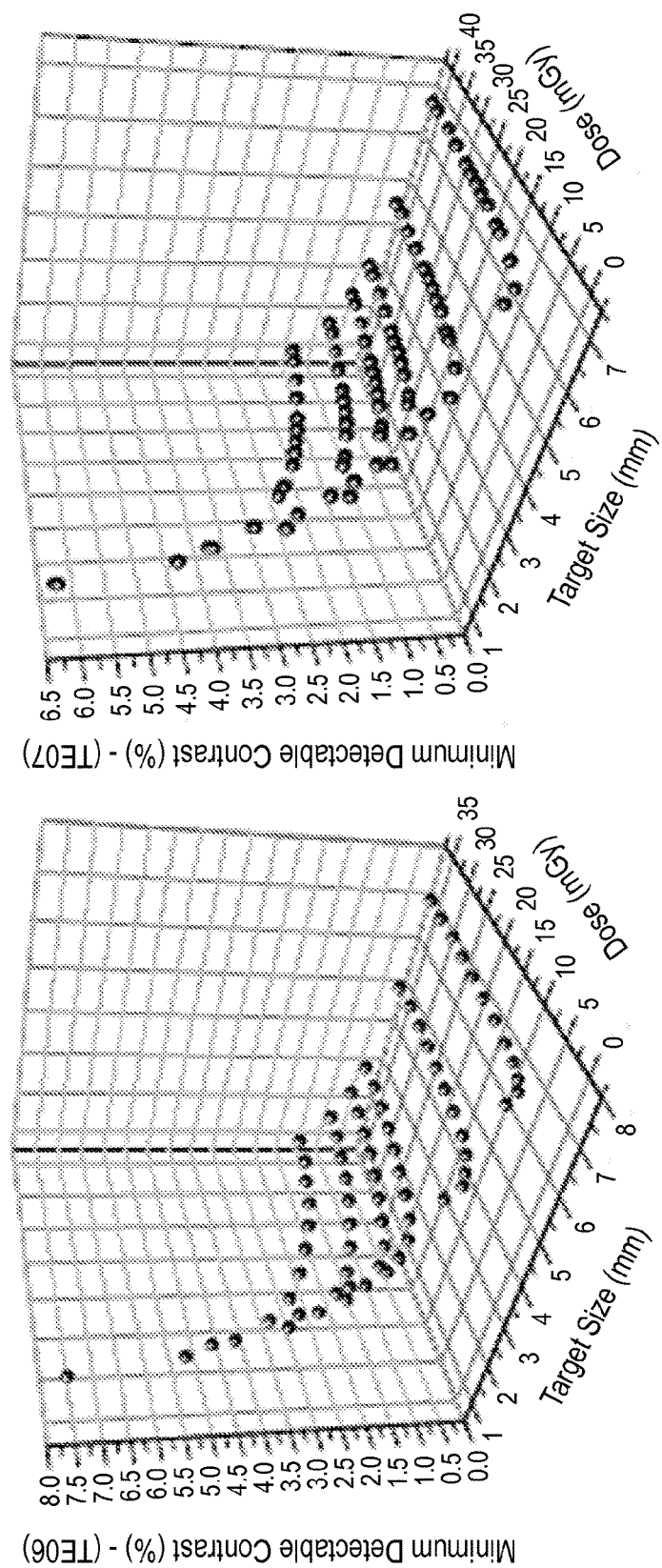
FIG. 18 illustrates graphs with results from scanning phantoms TE06 (left) and TE07 (right) using a GE HD750 CT machine, in accordance with aspects of the present disclosure.
Figure 19:
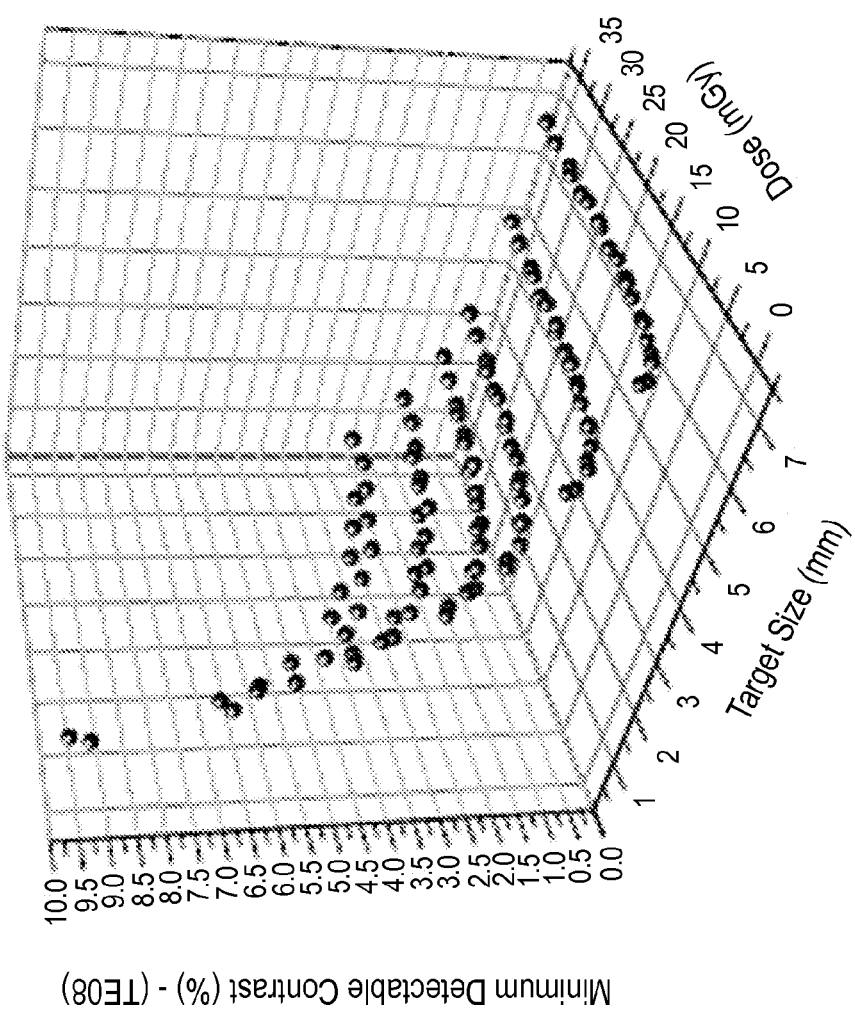
FIG. 19 illustrates a graph with results from scanning phantom TE08 using a GE HD750 CT machine, in accordance with aspects of the present disclosure.
Figure 20:
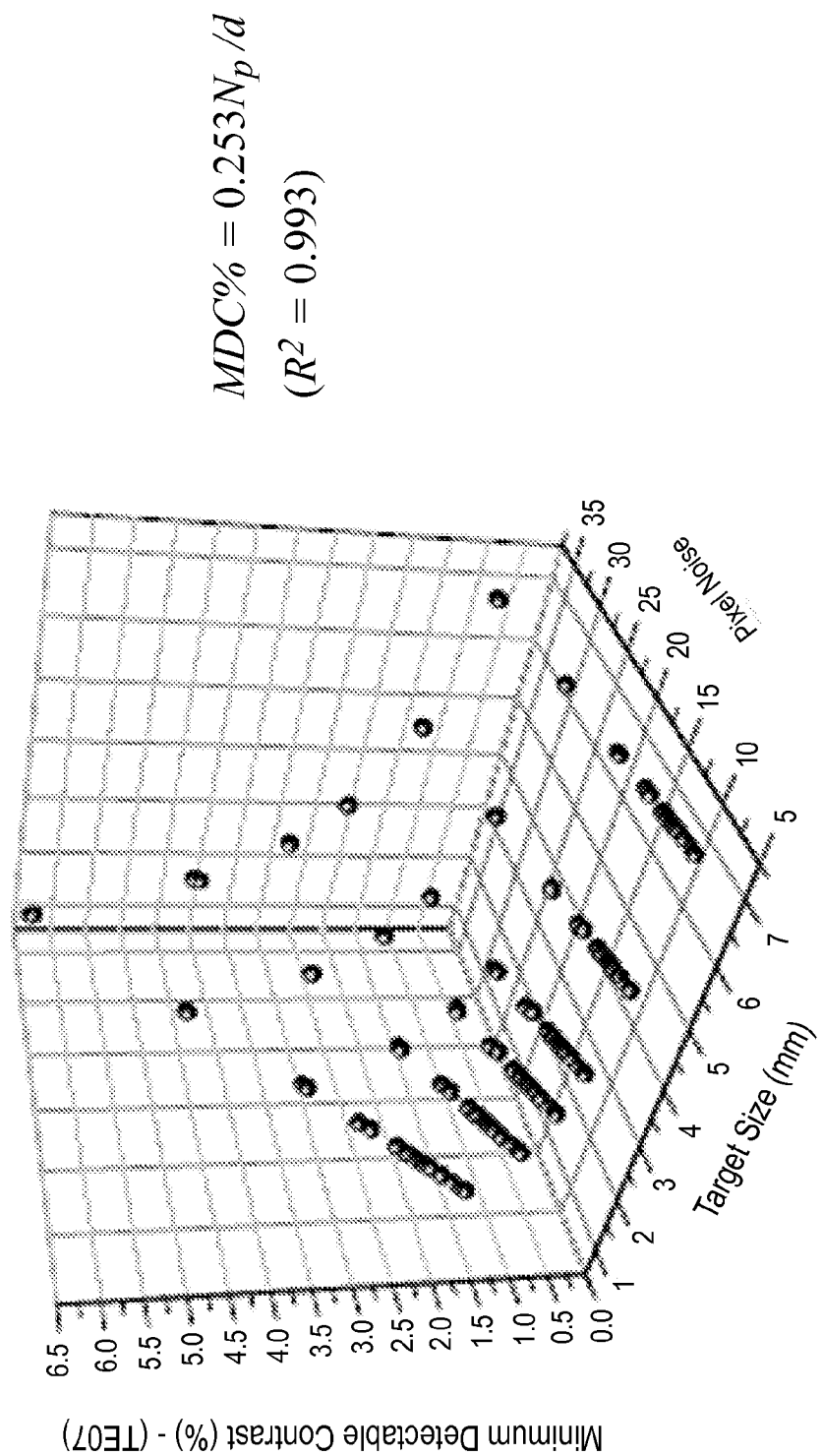
FIG. 20 illustrates a graph including correlations to pixel noise after scanning phantom TE07 (representing medium patient size) using a GE HD750 CT machine, in accordance with aspects of the present disclosure.

An exemplary validation based on the TE07 phantom scanned on the Siemens Sensation 64 machine is demonstrated in FIG. 14. Finally, a correlation of MDC to pixel noise is shown in FIG. 15, which can be used to convert MDC to noise to simplify task specific AEC implementation(s). Although this relationship was only validated on the TE07 phantom (medium size patient), one of skill in the art would readily appreciate that with further analysis it could be extended to other patient sizes.

Figure 21:
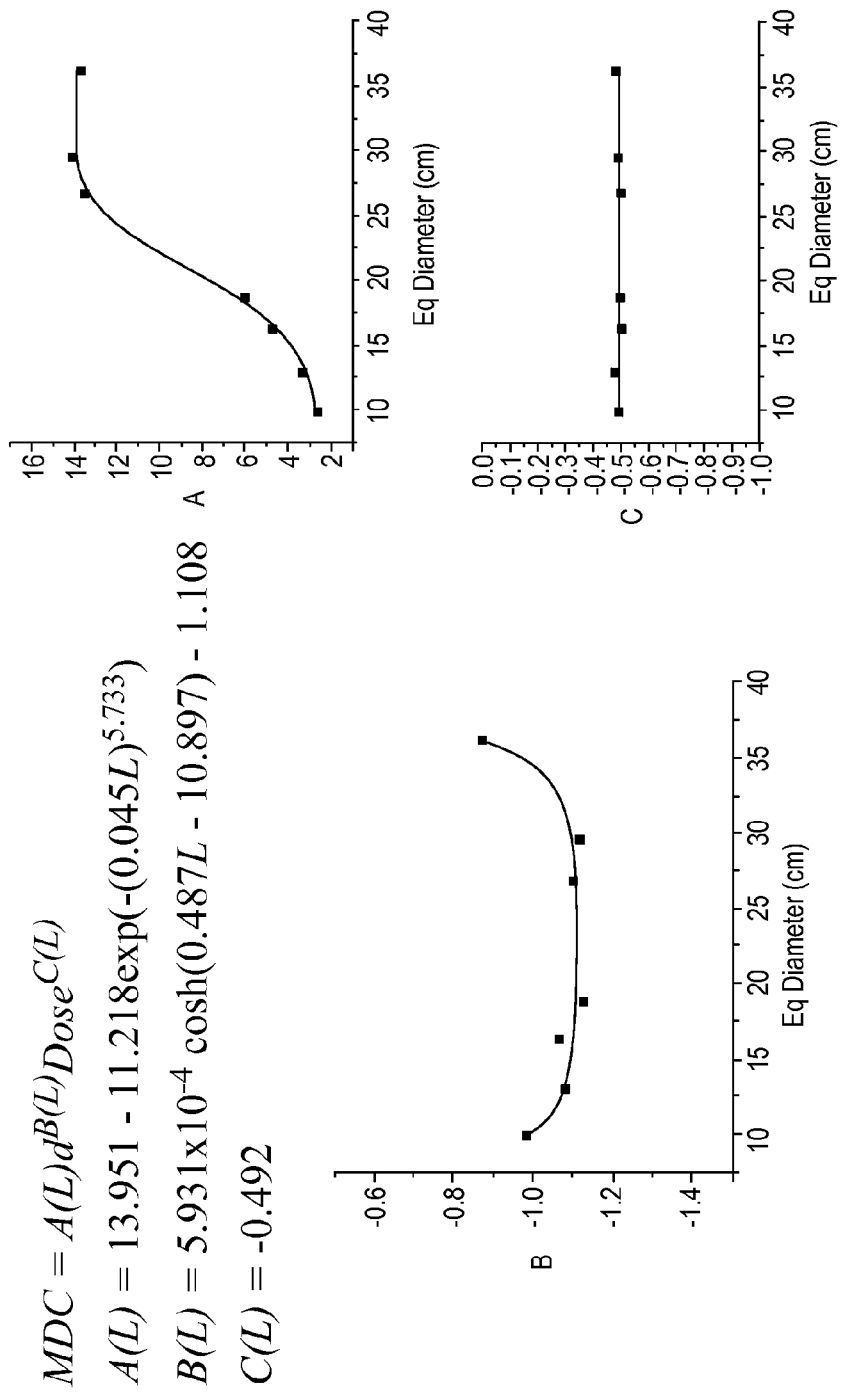
FIG. 21 illustrates graphs with exemplary fitting parameters vs. patient size for a GE HD750 CT machine, in accordance with aspects of the present disclosure.

For the CT scans performed using the GE HD750 machine, results are shown in FIGS. 16-19. An exemplary correlation of MDC to pixel noise for medium patient size (e.g., based on the TE07 phantom) is demonstrated in FIG. 20, which similar to FIG. 15 for the Siemens scanner, can be used to convert MDC to noise to simplify task-specific AEC implementation(s). Fitted parameters specific to the GE HD750 machine were then established as shown in FIG. 21. Errors using the power law model on MDC for the GE HD750 machine are shown in FIG. 22. Dose computation examples for the GE HD750 are shown in FIG. 23.

Referring now to FIG. 24, dose to techniques look-up curves were ascertained for the Siemens Sensation 64 and GE HD750 CT machines. It was also determined that patient size could be established from two-view scout images, as shown in FIG. 25. Additionally, center dose/weighted dose vs. equivalent diameter or Eq diameter for Siemens Sensation 64 and GE HD750 results are shown in FIG. 26 (left and right graphs, respectively).

It is contemplated that fitted parameters (e.g., A(L), B(L), and C(L)) can be developed and applied to other CT scanners similar to the process illustrated herein in FIG. 11 for the Siemens Sensation 64 and in FIG. 21 for the GE HD750 machines.

In order to obtain the appropriate acquisition techniques for a CT scan on a patient, (1) the desired contrast for the lesion size of interest in the patient is specified; (2) the two-view scout procedure described above is performed in order to determine patient size; and (3) the power-law model (described above for determining the minimum detectable contrast) is used to determine a patient- or subject-specific radiation dose. Appropriate acquisition techniques, such as the effective mAs (milli-ampere rotation time product divided by the pitch) can then be determined by using a previously obtained lookup curve.

In some aspects of the present disclosure, determining patient- or subject-specific dosimetry is desirable. For example, a ratio of center-weighted dose for various patient sizes can be determined using phantoms simulating abdomens of different sized patients. A relationship between patient size and dosimetry can then be experimentally determined by: (1) calibrating radiolucent dosimeters using ion chambers in phantoms (e.g., via Gafchromic film or Landauer dosimeters); (2) acquiring scout views in order to determine patient size using, for example, the methods above—e.g., see FIG. 25; (3) placing about two to four dosimeters on the surface of the patient (e.g., phantom) with one to two dosimeters placed laterally and one to two dosimeters placed antero-posterior; (4) performing CT scanning; and (5) obtaining patient specific weighted and/or center doses according to the relationships defined by:

$$\text{Dose}_c = \frac{2r}{3-r}\text{Dose}_p \quad (2)$$

and $$\text{Dose}_w = \frac{2}{3-r}\text{Dose}_p, \quad (3)$$

where $\text{Dose}_c$ is the center dose, $\text{Dose}_w$ is the weighted dose, $\text{Dose}_p$ is the peripheral dose, and $$r = \frac{\text{Dose}_c}{\text{Dose}_w}. \quad (4)$$

The ratio, r, for different patient sizes is obtained from the Gaussian relationships illustrated in FIG. 26 for center dose/weighted dose vs. equivalent diameter or Eq diameter based on the Siemens Sensation 64 and GE HD750 machines (left and right graphs, respectively).

One desirable aspect described by in present disclosure is that a statistically defined minimum detectable contrast (MDC) is related to the radiation dose, lesion size, and patient size in accordance with a power law and fitted parameters that can be customized, according the examples described herein for specific CT scanners. The two exemplary scanners illustrated herein are 64-slice scanners available from General Electric Company of Fairfield, Conn., USA (and its GE Healthcare subsidiary) and Siemens AG of Erlangen, Germany (and its Siemens Medical Solutions USA, Inc. subsidiary, of Malvern, Pa., USA). Thus, it has been shown that CT radiation dose can be lesion size specific and CT radiation dose can be patient size specific. The described power law model can be used to design a patient specific dose for a lesion specific task. One skilled in the art would readily appreciate that the same methodology can be extended to other scanners.

It is contemplated that in some aspects, images generated by a CT scanner can be reconstructed by applying filtered backprojection (FBP) techniques. A minimum radiation dose determined by this reconstruction may be described as an FBP minimum radiation dose. Some of the above describes techniques, such as those described in the context of FIGS. 3-26, can have the minimum radiation dose determined using FBP techniques.

As discussed in the present disclosure, systems and methods for quantitatively relating radiation dose to low-contrast detectability are desirable. Noise in CT is spatial frequency dependent. The contrast of various lesion sizes competes with the noise intensity at the matched spatial scales. Therefore, the statistical variation of noise at different scales can have a significant impact on the low contrast detectability. This property can be quantified by the statistically defined low contrast detectability (SF-LCD). In order to address the spatial correlation of the noise, SF-LCD can filter the noise in the image to different granularities according to the lesion sizes, and define the minimum detectable contrast at the corresponding spatial scales using the statistical nature of the noise. The measurable nature of SF-LCD and its direct connection to detectability can lead to the relationship of dose to lesion size and detectable contrast. It would be desirable to know about the relationships of radiation dose to lesion size and detectable contrast.

The SF-LCD can be based on an assumption that the target of a certain size can only be differentiated from the background if its contrast exceeds the noise at the same spatial scale by a certain amount. For a noisy image with uniform background, the noise texture may be obtained in the following manner. A relatively large region in the interested area is partitioned to a matrix of squared elements of a certain size. The mean pixel value from each element is computed. If the noise only originates from random photon fluctuations, the distribution of the mean values is expected to be Gaussian according to the Central Limit Theorem and the noise can be quantified by the standard deviation.

Additional experimental methods and results are discussed in more detail below including validation data results that are presented and discussed below in the context of FIGS. 27-39. In certain aspects, the validation results demonstrate minimum radiation dosages determined by the power law model result in at least a 93 percent confidence level of 5-mm to 7-mm lesion targets being identifiable. The validation results are close to the 95 percent confidence level of 5-mm to 7-mm lesion targets being identifiable that was predicted by the noise mean value distributions.

Figure 27:
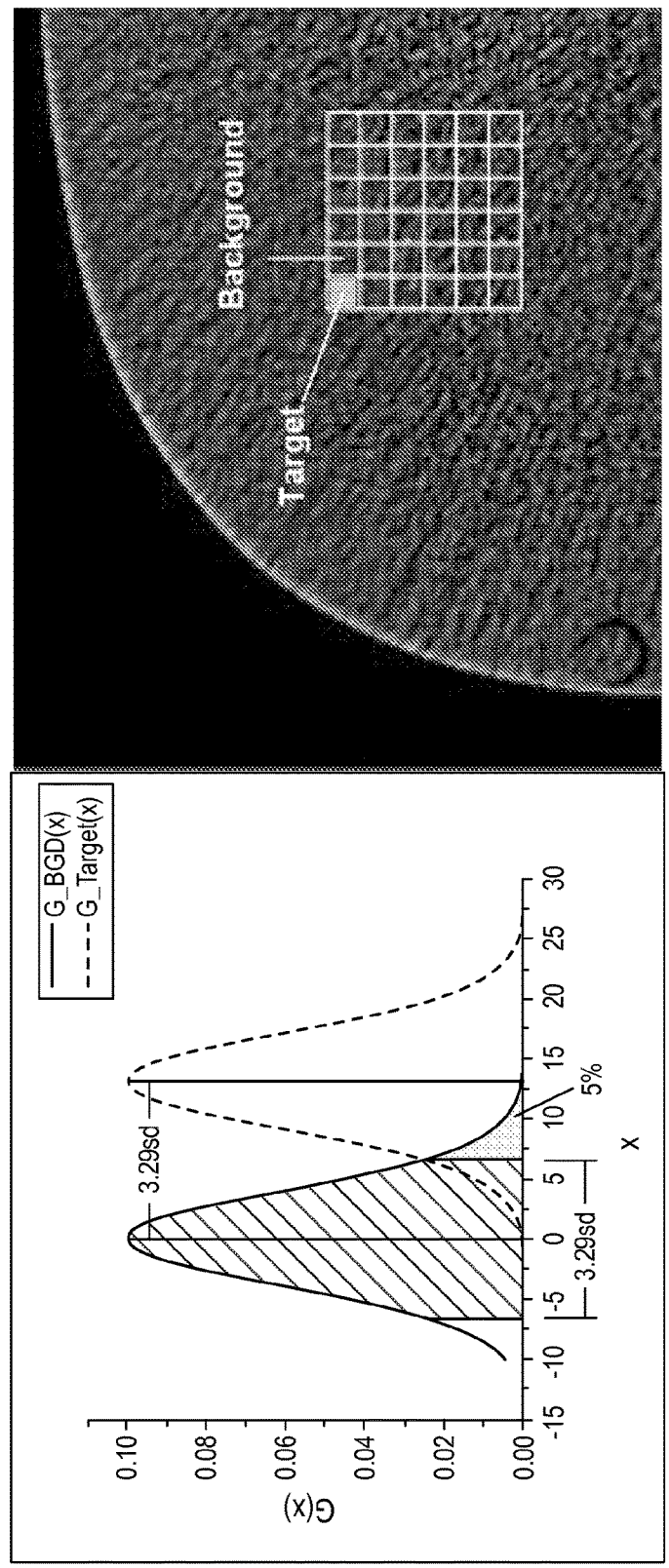
FIG. 27 illustrates an exemplary statistically defined low contrast based on the separation of the means distribution of a target (the curve on the right) from that of the background (the curve to the left), in accordance with aspects of the present disclosure.

FIG. 27 illustrates an aspect of statistically defined low contrast detectability. For example, a target of an element size may be placed across the same region. The distribution of the target pixel mean values will be of the same shape but needs to be shifted from that of the background pixel mean values by a certain amount in order for the target to be differentiated. If the distribution is Gaussian, the minimum shift required for differentiation with 95% confidence level is given by the standard deviation multiplied by 3.29. The minimum shift is called minimum detectable contrast (MDC). These exemplary aspects are illustrated further in FIG. 27, which demonstrates a statistically defined low contrast given by the separation of the means distribution of the target from that of the background. The process can be repeated for different target sizes.

A relationship of the MDC to dose and lesion size can be formulated as follows. For reconstructions using FBP, the variance at center of the image can be written as:

$$\sigma^2(0,0) = \frac{\pi^2(\Delta\xi)^2}{N_p\langle n(0)\rangle}\left(\sum_{k=-D/2}^{k=D/2} g^2(k\Delta\xi)\right) \quad (5)$$

where $\Delta\xi$ is the detector element width, $N_p$ is the number of projections, $\langle n(0)\rangle$ the average number of X-ray photons detected by the center element, D the number of detectors, and g the reconstruction kernel. In some aspects, it can further be estimated that the lesion size dependent contrast-to-noise ratio (CNR) is as follows $$CNR(d) = \frac{d^f \Delta\mu}{\sigma} \quad (6)$$

where d is the linear size of the lesion, $\Delta\mu$ the pixel contrast in terms of attenuation coefficient, and f the power index to be determined.

In some aspects, it may be preferable for the minimum detectable pixel contrast (MDC) in the above CNR of equation (6) to exceed a certain threshold K. Given that the product $N_p\langle n(0)\rangle$ is proportional to the dose, the MDC follows $$MDC \propto \frac{\Delta\xi \exp(\mu L/2)}{d^f \cdot \sqrt{Dose}}\left(\sum_{k=-D/2}^{k=D/2} g^2(k\Delta\xi)\right)^{1/2} \quad (7)$$

where L is the patient size. The above formulation in equation (7) is for the center of the image. However, for the same scanner and a known patient size, the following power law can apply for the images reconstructed with filtered backprojection (FBP):

$$MDC\ (\%) = A d^B Dose^C \quad (8)$$

where A, B and C are the coefficients to be experimentally determined and can be considered fitted parameters particular to a specific CT machine.

In order to see the change of MDC in response to dose, the following can be derived based on equation (8):

$$\partial(MDC)/\partial(Dose) = C A d^B Dose^{C-1} \quad (9)$$

Noise characteristics in a scanner are typically scanner design dependent. In some aspects of the experimental undertakings and validations for medium-sized phantoms (e.g., TE07) described below and in the context of FIGS. 28-39, testing was conducted using two multi-slice (64 slices) CT scanners of different makes. The first was a CT from a Siemens Biograph mCT (software version syngo MI.PET/CT 2009C, Siemens Healthcare, Erlangen, Germany) and second a GE Discovery 750 HD (software version gmp_hde.74, GE Healthcare, Waukesha, Wis., USA). The Siemens scanner is equipped with double sampling (flying focal spot) technology along the longitudinal direction. The detector element width and total detector width at the isocenter are 0.6 mm and 19.2 mm, respectively. The focal spot to detector distance is 1085 mm. The GE scanner is equipped with the Gemstone detector and fast kV switch technology for spectral imaging. The detector element width and total detector width are 0.625 mm and 40 mm, respectively. The focal spot to detector distance is 946 mm.

Figure 28:
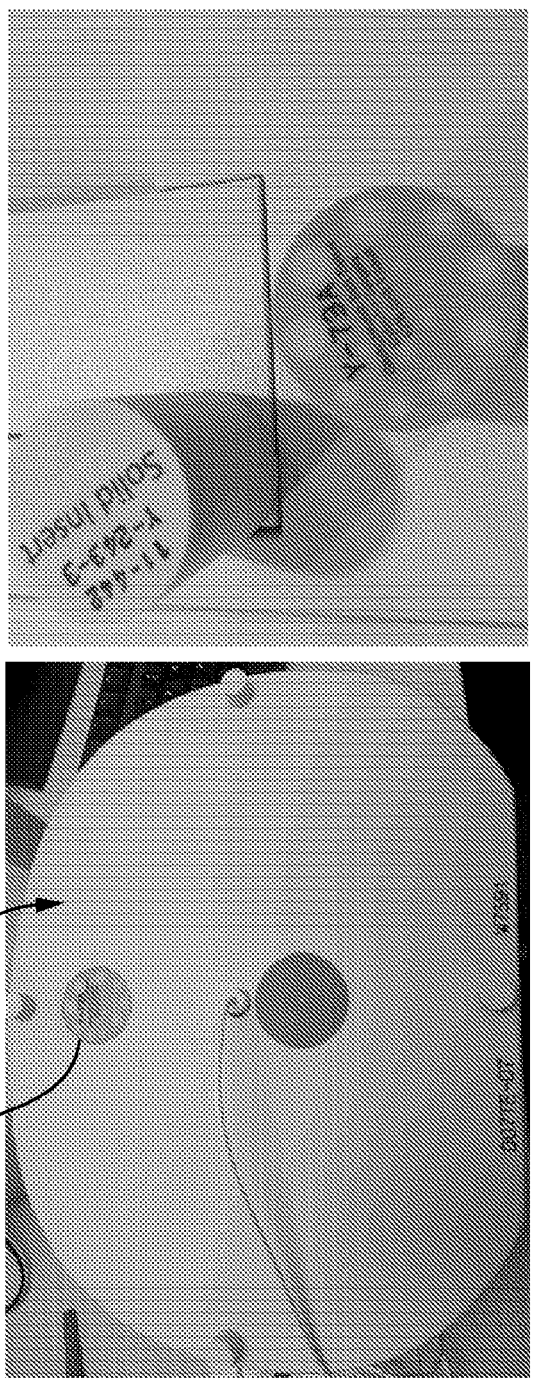
FIG. 28 illustrates a computer tomography abdomen phantom with low contrast inserts, in accordance with aspects of the present disclosure.

FIG. 28 illustrates a realistically shaped exemplary abdomen phantom (CIRS TE-07, CIRS, Norfolk, Va., USA) that was used in for the testing. The phantom is of a medium-sized abdomen customized for the low contrast insert. The phantom is tissue equivalent and is embedded with a vertebral bone rod to simulate the X-ray interaction similar to that in the medium sized adult patient. The dimensions are 25 cm (anterior-posterior)×32 cm (lateral)×15 cm (longitudinal). A cylindrical void of 4 cm in diameter was customarily drilled through the phantom above the center. The void was filled at the longitudinal center with a low contrast insert (CIRS 700 QA) and the rest with the solid insert of the same phantom material. The low contrast insert is 5-cm long and contains six groups of cylindrical targets (nominal contrast 1% and 2%) sized from 1.2 mm to 7 mm. Each group contains three targets of the same size. There are five 1-cm holes (four at the periphery and one at the center) for onsite dose measurements.

In the described exemplary experimental tests, the exemplary phantom described for FIG. 28 was centered in each of the two scanners (e.g., the Siemens and the GE scanner). To account for the scatter from the adjacent anatomy, two similar phantoms were placed on the superior and inferior sides. Helical scans were performed at 120 kVp with collimations of 32×0.6 mm and 64×0.625 mm, for the Siemens Biograph 64 and for the GE 750 HD scanners, respectively. For both scanners, the scan field of view was 50 cm and the reconstructed field of view was 35 cm. The slice thickness was 5 mm with reconstruction kernels of B30f and "standard", for the Siemens Biograph 64 and GE 750 HD, respectively. The two reconstruction kernels are contemplated to match closely in terms of the noise properties. The corresponding pitches were 1.4 and 1.375. The milli-ampere-second (mAs) values were adjusted from 37.5 to 630 (15 dose levels) and from 35 to 595 (14 dose levels), for the Siemens Biograph 64 and the GE 750 HD, respectively.

For each scanner, the dose measurement similar to $CTDI_{vol}$ was made on the phantom in the following manner. A 10-cm ion chamber (Radcal 10×5-10.3CT, Monrovia, Calif., USA) was placed at the phantom center and four periphery holes. At each position, an average air kerma was obtained from three measurements under axial scans with 120 kVp, 200 mAs and the fully opened collimation. The weighted CT dose was obtained using the weighting factors of ⅓ and ⅔ for the center and peripheries, respectively. The volume CT dose from each helical scan was computed by dividing the weighted dose by the pitch.

For each scan conducted during this exemplary testing, there were ten slices covering the low contrast insert in the longitudinal direction. Eight interior slices were chosen for subtractions between the consecutive slices to remove the DC component in the noise. For each of the six exemplary target sizes (7 mm, 5 mm, 3.5 mm, 2.5 mm, 1.8 min and 1.2 mm), four matrices with the matched element size were applied at four areas of 41 mm×41 mm. Because of the image pixel digitization, the element size of each matrix may not exactly equal to the insert target size, but the closest match was chosen.

Figure 29:
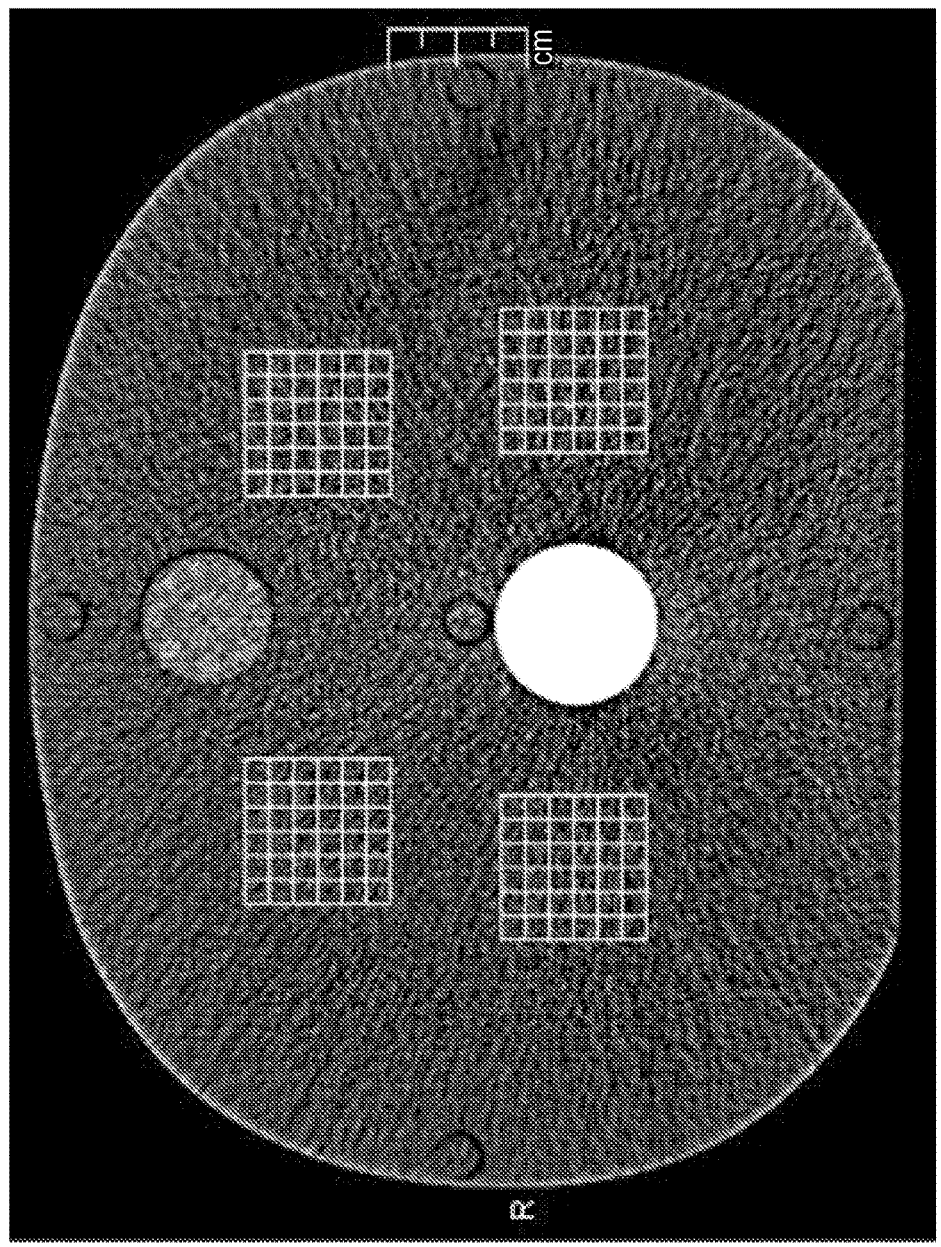
FIG. 29 illustrates exemplary matrices whose element size matches 7 mm before a slice subtraction, in accordance with aspects of the present disclosure.

FIG. 29 illustrates the exemplary matrices whose element size matches 7 mm before the slice subtraction for the exemplary medium-sized phantom (e.g., TE07). The total number of elements in the four matrices was 144, 256, 576, 1156, 2116 and 4900, for the target sizes of 7 mm, 5 mm, 3.5 mm, 2.5 mm, 1.8 mm, and 1.2 mm, respectively. For each subtracted image, the element mean pixel values were calculated from the four matrices at each element size and the mean values distribution was obtained. The final distribution of the means was obtained by averaging the results from the seven subtracted images. The procedure was applied to the images acquired from both scanners and was completed through the use of a computer algorithm that included instruction for performing the above actions.

Given the number of the elements (144 to 4900), a Komogorov-Smirnov normality test was selected to examine all distributions using OriginPro 8.1 (Northampton, Mass., USA). This normality test provides two parameters, the test statistic, D, describing the difference in the cumulative distribution function (CDF) from that of the ideal normal distribution, and the p-value characterizing the significance of the difference. If the p-value is smaller than the pre-determined alpha level, say 0.05, it is contemplated that the Gaussian distribution assumption would be rejected.

For each distribution determined from the FBP reconstructed images, after being verified to be a Gaussian, the standard deviation among the means was multiplied by $\sqrt{2}$ to correct for the slice subtraction. The result multiplied by 3.29 (e.g., as determined in FIG. 27) can then serve as the minimum detectable contrast (MDC). For each dose level and target size, the MDC was obtained in such a manner. Equation (8) can then be applied to obtain the fitting parameters, A, B, and C.

In some aspects of CT scanners, pixel noise is used for dose modulation. However, a typical issue arises from the pixel noise being variably prescribed, causing patient dose variation. If the pixel noise is derived from the required MDC and lesion size, the dose modulation scheme can be adapted to be task specific. Since for CT images reconstructed with FBP, the dose can be determined by the pixel noise in the following form $$\text{Dose} \propto 1/\text{Noise}^2 \quad (10)$$

The MDC versus the dose and target size relationship can then be derived from equations (8) and (10) as $$\text{MDC} = G d^K / \text{Noise}^M \quad (11)$$

where G is a proportionality factor.

To obtain the pixel noise for each set of the subtracted slices at each dose level, the mean standard deviation was obtained from the exemplary four regions of interest identical to the areas for the MDC analysis. The average pixel noise among all subtracted slices was calculated. The MDC was plotted against the average pixel noise and target size, and equation (11) was used for fitting to find G, K and M. The K and M are expected to be consistent with the fitting parameters described above in the following manner:

$$K = B \quad (12)$$

$$M = -2C \quad (13)$$

In some aspects of the described exemplary experiments, low contrast images were mixed with images without contrast signals and were randomly presented to experienced readers of CT scans. The images were made anonymous and the technique display was removed. The 5 mm-7 mm targets were scored independently by three radiologists and two medical physicists, who did not have the knowledge of the image arrangement, but were experienced in reading CT images. The window level and width were set at 50 and 350, respectively. The viewer distance to the monitor was between 30 cm-35 cm. The scoring was conducted on a three-point Likert scale. Each clearly depictable target was scored 1. Each just recognizable target was scored 0.5. The target was scored 0 otherwise. For each target group, if the score is 1 or higher, it is defined as detectable.

Figure 30:
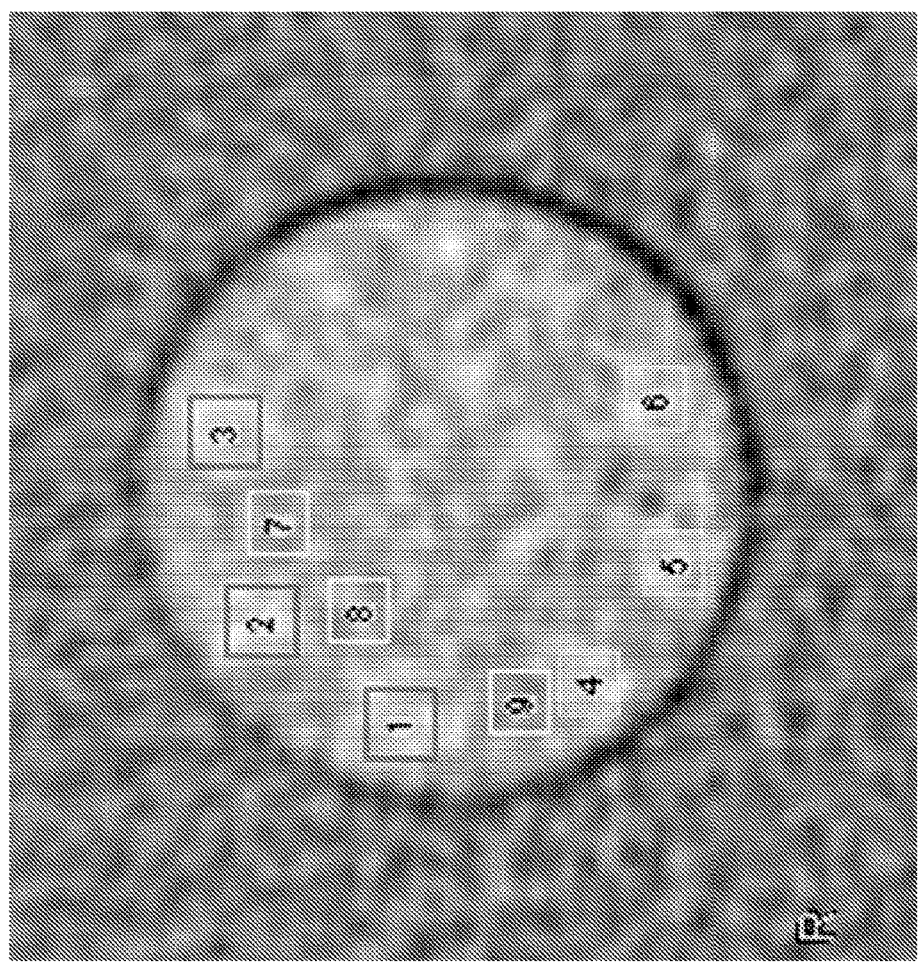
FIG. 30 illustrates exemplary selected regions for signal and background measurements, in accordance with aspects of the present disclosure.

The local contrast for the 5 mm and 7 mm targets in the above slices were measured. The locations of the measurement regions were identified using the images acquired with high doses as shown in FIG. 30. Regions 1, 2 and 3 (size of 5×5 pixels) and regions 4, 5 and 6 (size of 3×3 pixels) were used for the 7 mm and 5 mm targets, respectively. Regions 7, 8, 9 (size of 3×3 pixels) were used for the background near the 7 mm targets. The minimum detectable contrast was obtained using equation (8). Care was taken to convert the circular target size to the area equivalent square size. The measured contrast was divided by the minimum detectable contrast and the resulted contrast ratio was then correlated with the target score.

Weighted CT dose was measured in the range of 2.0 mGy to 34.0 mGy (15 levels), and 2.3 mGy to 38.3 mGy (14 levels), for scanners A and B, respectively. The weighted CT dose values per 100 mAs are listed in Table 1 (see FIG. 31). The center to periphery dose ratios are also included in the table. Manufacturer names are not specified to be impartial to the results. The same convention of applying the generic terms Scanner A and Scanner B was applied in the below discussions.

Figure 32:
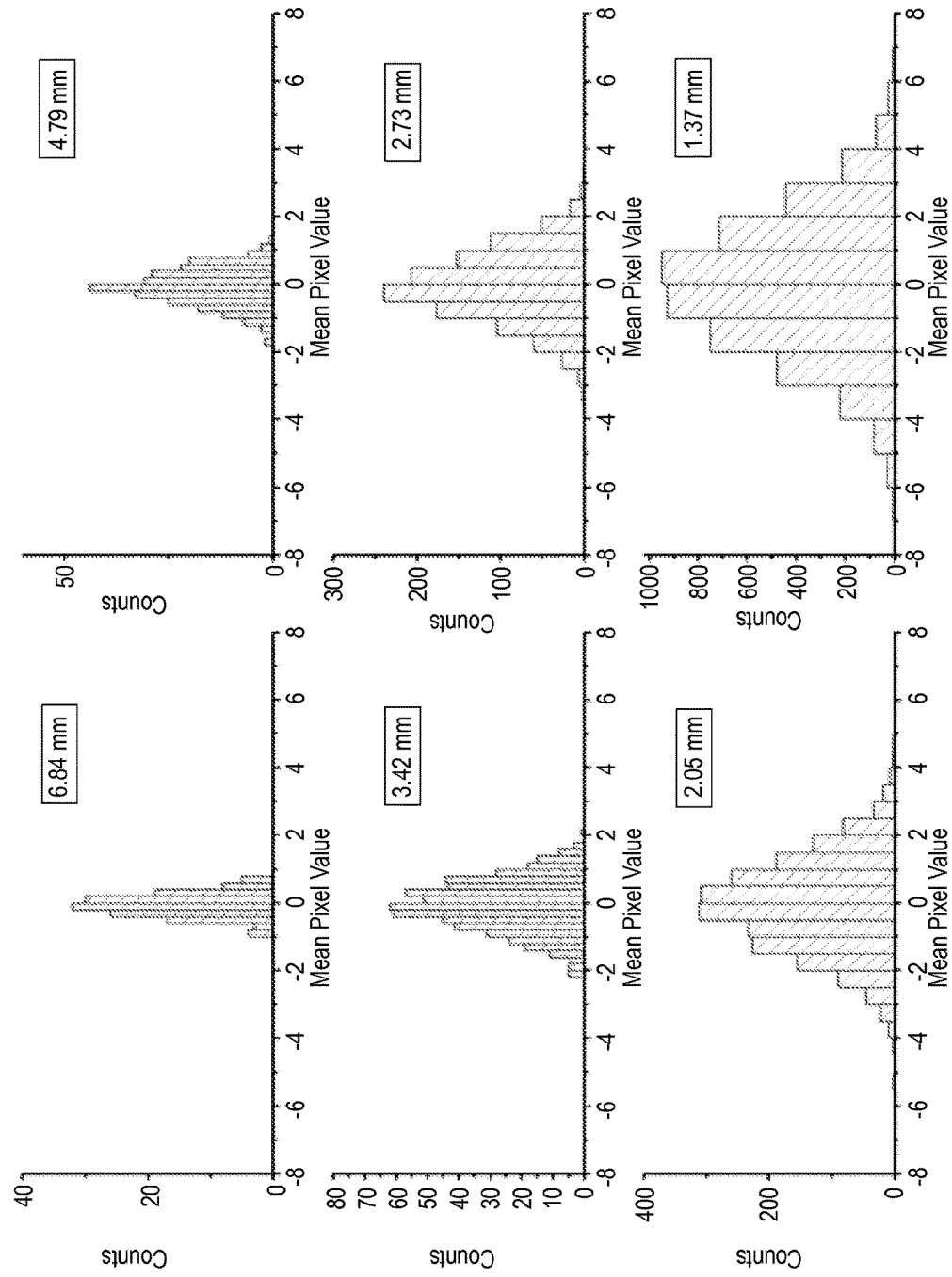
FIG. 32 illustrates mean pixel value distributions for different element sizes at a weighted dose of 16.4 mGy on either the GE 750HD or the Siemens Biograph 64 scanners, in accordance with aspects of the present disclosure.
Figure 33:
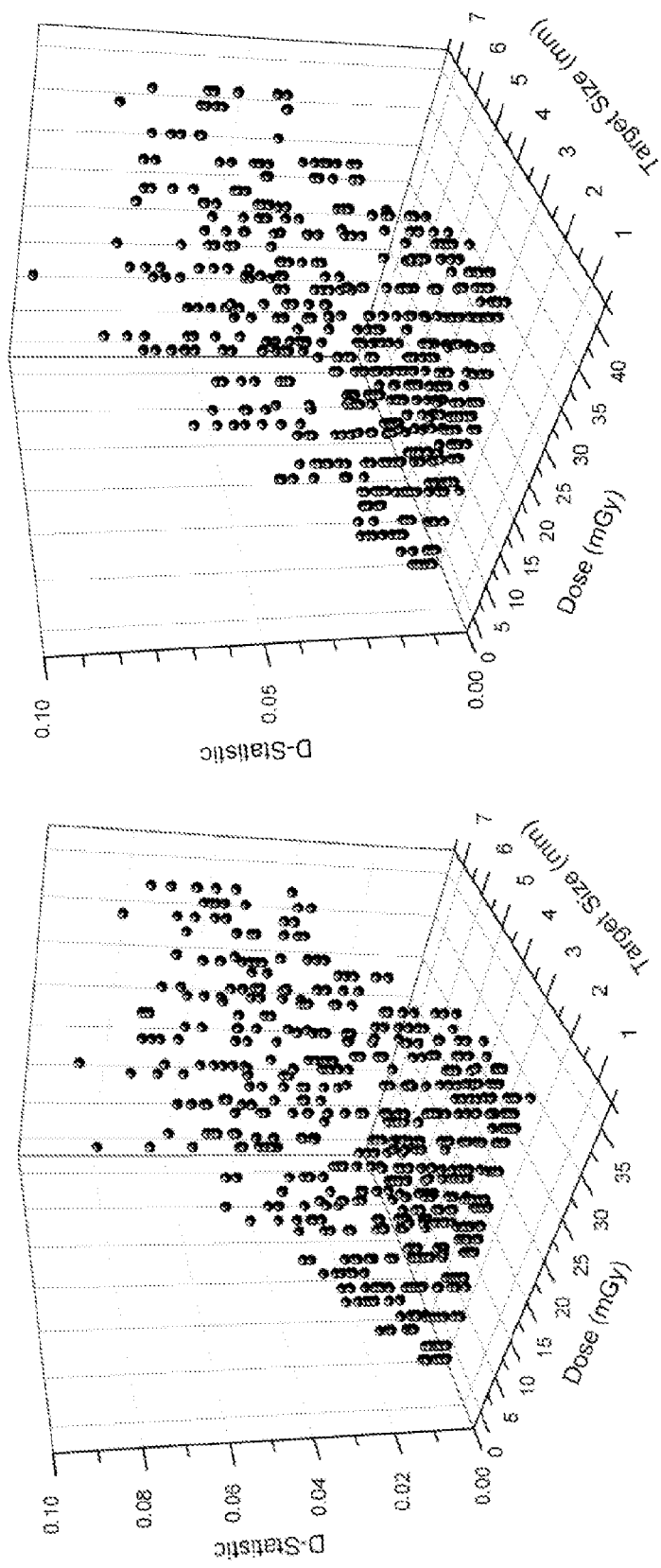
FIG. 33 illustrates exemplary D-statistic results for a Komogorov-Smirnov test for scanners A (left) and B (right), in accordance with aspects of the present disclosure.
Figure 34:
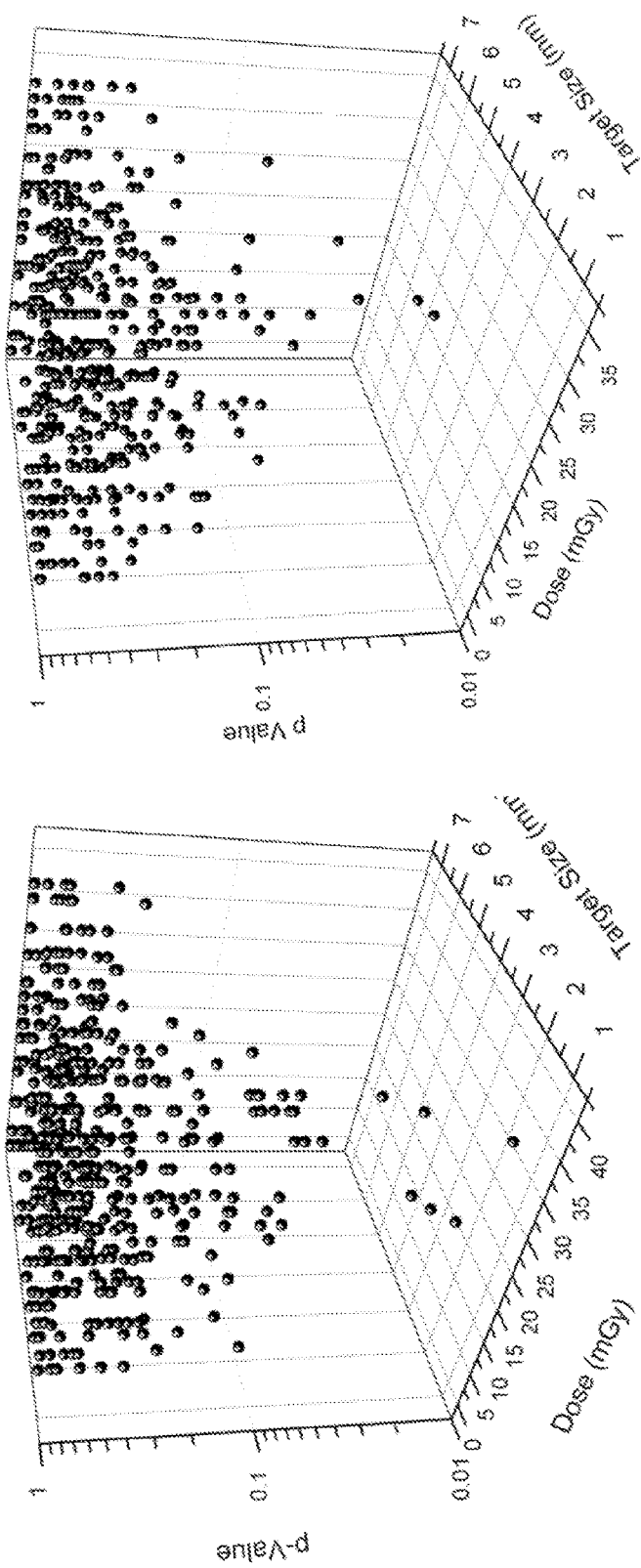
FIG. 34 illustrates exemplary p-value results from a Komogorov-Smirnov test for scanners A (left) and B (right), in accordance with aspects of the present disclosure.

FIG. 32 illustrates plots of the mean pixel value distributions for different element sizes obtained from the FBP reconstructed images at the weighted dose of 16.4 mGy on one of the scanners. The distribution widens as the element size decreases, demonstrating lower detectability of smaller targets. The normality test results for all subtracted slices reconstructed with FBP at different dose levels are illustrated in the graphs shown in FIGS. 33 and 34 (630 and 588 data points, for scanners A and B, respectively). FIG. 33 shows the D-statistic results for Komogorov-Smirnov test for scanner A (Siemens, left) and B (GE, right). FIG. 34 shows the corresponding p-values. Except for two data points from scanner A and five from scanner B, the results showed that at the 0.05 level, the distributions are significantly drawn from Gaussian.

Figure 35:
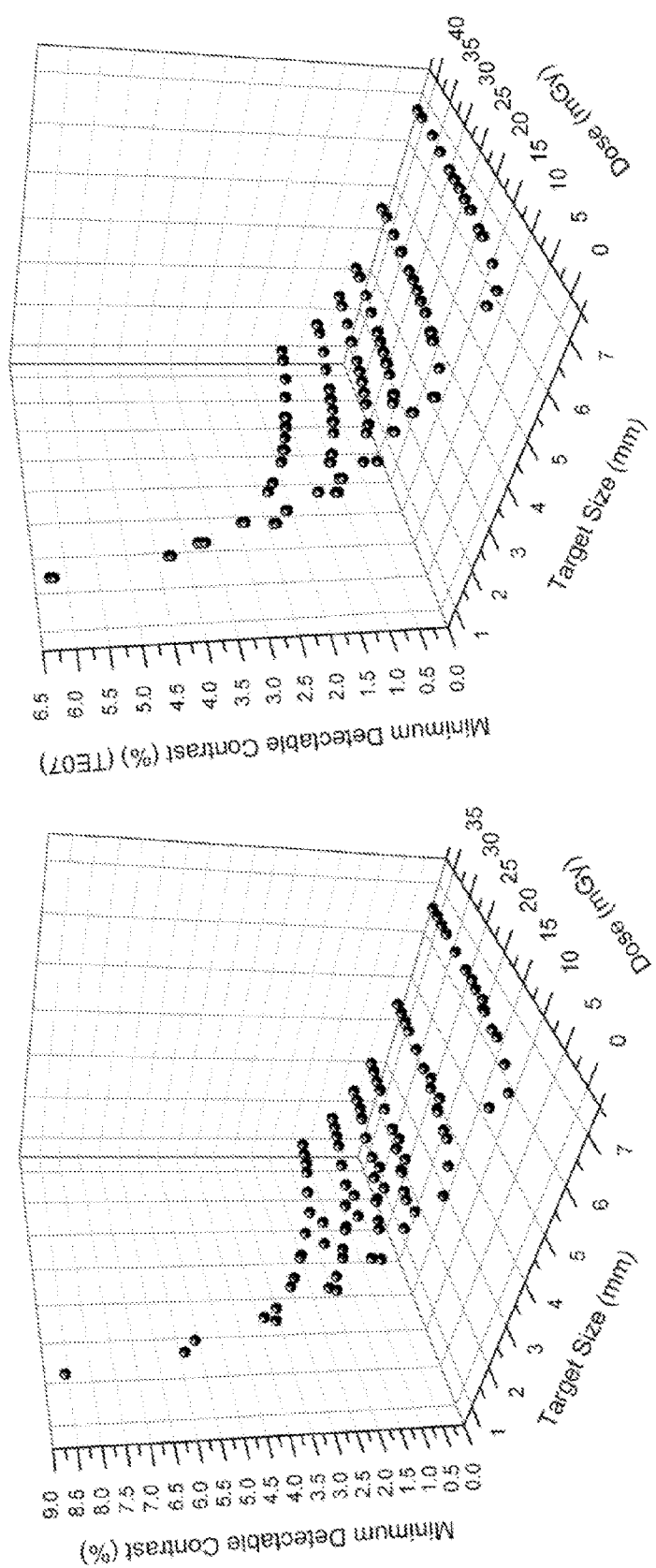
FIG. 35 illustrates graphs showing results of a minimum detectable contrast versus dose and target size for scanners A (left) and B (right), in accordance with aspects of the present disclosure.

Referring now to FIG. 35, the minimum detectable contrast is plotted against the measured dose and target size for the FBP reconstructed images with the scanner A results in the graph to the left and the Scanner B results in the graph to the right. The errors bars are not shown in the figure due to the 3D graphing limitation, but the average errors were 4.0% and 3.6%, for scanners A and B, respectively. The fitting parameters using the power law model in equation (8) are listed in Table 2 (see FIG. 36), and reflect an exemplary case related to FIGS. 11 and 21 for a patient of medium size. The results demonstrate that the minimum detectable contrast decreases as the target size or the dose increases. It is noted that the power index for the target size is close to −1, whereas the power index for the dose is close to −0.5. The correlation coefficients in these exemplary aspects were found to be 0.993 and 0.999, for scanners A and B, respectively.

Figure 37:
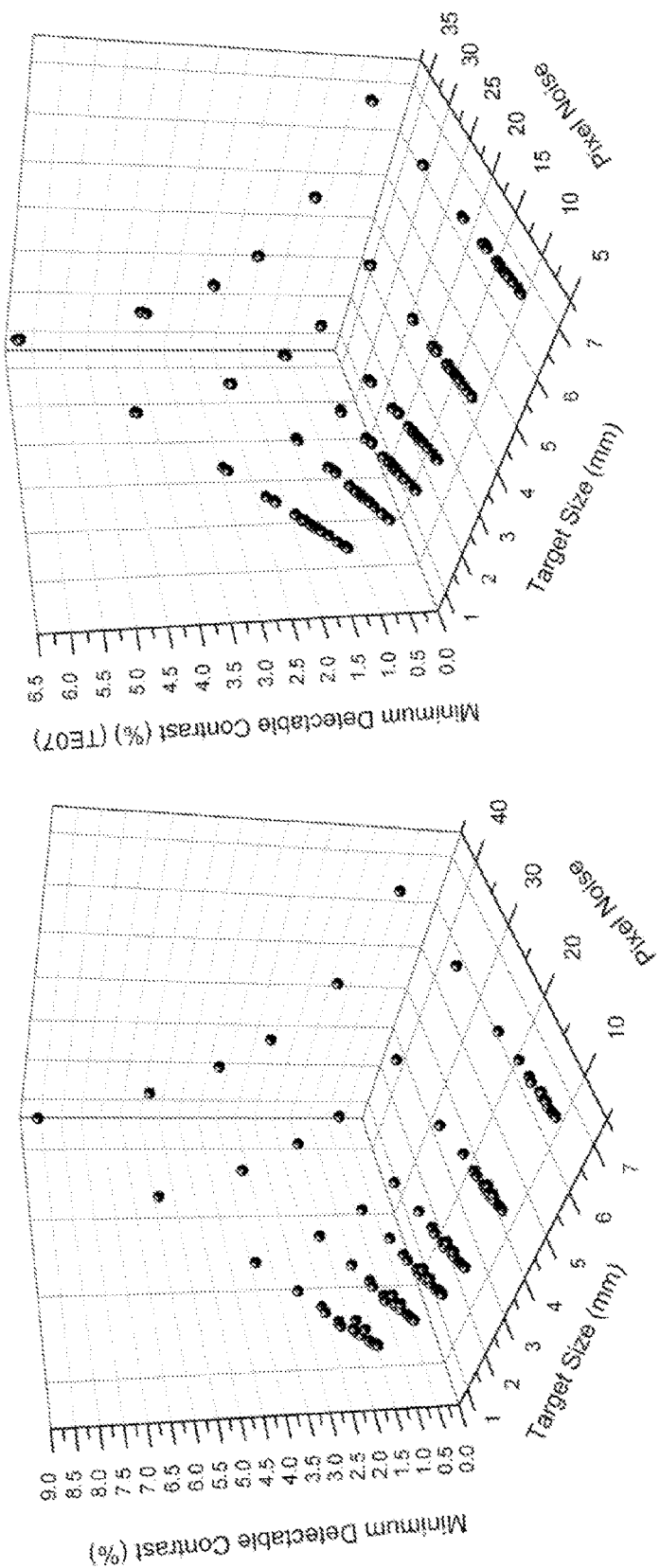
FIG. 37 illustrates graphs with results showing minimum detectable contrast versus the pixel noise and target size for scanners A (left) and B (right), in accordance with aspects of the present disclosure.

Referring now to FIG. 37, the minimum detectable contrast is plotted in two graphs against the pixel noise and target size for scanners A (Siemen, left graph) and B (GE, right graph). Error bars, again, were not shown due to the 3D plot limitation. Average errors for these exemplary aspects were 4.0 percent and 3.6 percent, for scanners A and B, respectively. It is seen that the minimum detectable contrast increases nearly linearly with the pixel noise. The fitting parameters using equation (11) are listed in Table 3 (see FIG. 38). The correlation coefficients were found to be 0.994 and 0.999, for scanners A and B, respectively. The parameters K and M in Table 3 (see FIG. 38) and parameters B and C in Table 2 (see FIG. 36) were found to be consistent with equations (12) and (13). The differences in percentage are 5.4% and 2.0% for M, and 0.3% and 0.3% for K, respectively, for scanners A and B.

Figure 39:
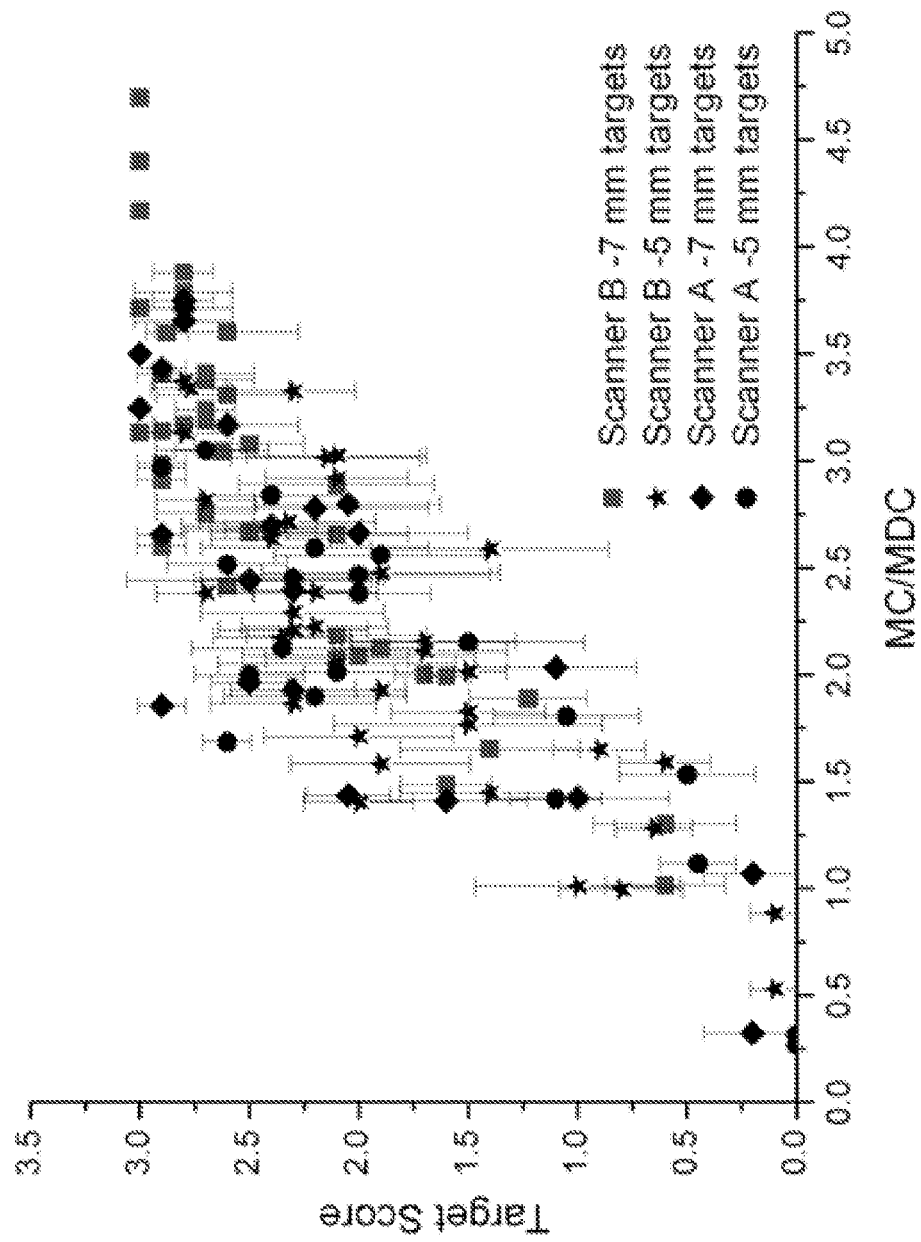
FIG. 39 illustrates a graph of reading scores versus the ratios of the measured contrast to the minimum detectable contrast for the exemplary 7-mm and 5-mm targets, in accordance with aspects of the present disclosure.

Referring now to FIG. 39, the results from reading scores determined as discussed above were plotted against the ratios of the measured contrast to the minimum detectable contrast for the 7-mm and 5-mm targets. There were 123 sets of image data from both scanners including some repeated scans. The repeated scans have the same minimum detectable contrast but the measured contrast and the score may vary slightly due to the signal fluctuation. As shown in FIG. 39, there is a meaningful correlation between the target score and the minimum detectable contrast (Pearson coefficient=0.834). Among 118 cases where the measured contrast exceeds the minimum detectable contrast, there were 109 cases where the targets were scored detectable. This results in a 93 confidence level, which is close to but slightly lower than the predicted 95% confidence level.

Systems and methods for the optimization of images are desirable particularly as radiation dosage is constrained by the image quality requirement. It is further contemplated that systems and methods for quantifying image quality are also desirable for image optimization. The system and methods described in the present disclosure provide exemplary non-limiting aspects for image optimization for abdominal CT scans and provide a solution to determining minimum radiation dosages to detect lesions of a certain size, patient or subject size, and contrast.

In some aspects, the power law postulated in equation (8) about the minimum detectable contrast to dose and lesion size provides desirable information for improving image optimization while reducing radiation dose in CT scans. The power index to dose close to −0.5 shows that the minimum detectable contrast does not reduce linearly as the dose increases. Equation (9) shows that the MDC change rate with respect to dose is proportional to $Dose^{-3/2}$, indicating that for the same amount of dose increase, the image quality improvement is much less significant in the higher dose range. For example, for a circular lesion size of 7 mm, a delivery of 15 mGy dose generates the minimum detectable contrast of 0.5% for scanner B. As a comparison, a dose of 42 mGy only improves the minimum detectable contrast to 0.3% for the same scanner.

In some aspects, it may be desirable to look at the relationship of the minimum detectable contrast to the pixel noise and target size. Given that the square of the pixel noise is directly proportional to the integral of the noise power spectrum, the nearly linear relationship of the MDC to the pixel noise shows that the dose impact to all frequency components in the noise power spectrum is the same. In the meantime, the nearly inverse linear relationship of the MDC to the target size implies the noise power spectrum is a quadratic function in the spatial frequency range of the study. Furthermore, as shown in Table 3 (see FIG. 38) the relationship is not sensitive to different scanners. This may be explained by the same dependence of the gross (pixel) noise and noise texture on the scanner specifics (e.g., the number of projections, the design of a bowtie filter, the detector).

While the relationships have been described for some aspect of the present disclosure based on an exemplary medium-sized, abdomen phantom, it would be expected that the same patient size dependency of the gross noise and of the noise texture where it may still remain valid for different patient sizes. The advantage of the relationship is that the pixel noise can be derived from the specific detectability requirement, which in turn serves as a noise index for dose modulation. For example, a 7-mm circular target with 0.5% minimum detectable contrast requires a pixel noise (noise index) of 10.5 and 11.2, respectively, for scanners A and B. By comparison, a 5-mm circular target with 0.5% minimum detectable contrast will require a noise index of 7.5 and 8, respectively, for scanners A and B.

It is contemplated that the aspects described in the present disclosure may be applicable to CT scanners others than those specifically identified and may further be applicable for different slice widths and different sized patients (represented by phantoms).

A desirable relationship of minimum detectable contrast to the patient dose and the lesion size is described. The derived minimum detectable contrast was found consistent with the scoring results of the inserted low contrast targets. The relationship of the minimum detectable contrast to the pixel noise was also studied and was found to be invariant to different scanners. The current pixel noise based dose modulation can be adapted to be task specific through the relationships described by the present disclosure.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A computed tomography (CT) imaging system for imaging a body region of a subject, the system comprising:
   CT scanner circuitry including one or more processing units and one or more memory devices, the one or more memory devices storing instructions that, when executed by at least one of the one or more processing units, cause the CT scanner circuitry to implement the acts of:
   receiving first input data indicative of a lesion size of interest,
   receiving second input data indicative of a predetermined minimum detectable contrast (MDC),
   receiving third input data associated with a size of a subject being imaged,
   determining a value for the size of the subject based on the received third input data, and
   determining a radiation dose to apply to the subject, the determining of the radiation dose based on a power law model relating size of the subject, lesion size, and minimum detectable contrast, the power law model defined as $MDC=A(L)d^{B(L)}Dose^{C(L)}$, wherein (i) MDC is the predetermined minimum detectable contrast, (ii) d is the lesion size, (iii) Dose is radiation dose, (iv) A(L), B(L), and C(L) are pre-determined fitted parameters for the CT imaging system, and (v) L is the determined value for the size of the subject;
   a radiation source configured to rotate about the body region of the subject, the radiation source configured to emit the determined radiation dose; and
   a radiation detector for sensing radiation doses emitted from the radiation source, the detector generating electronic signals in response to the sensed radiation doses, the electronic signals representing image data received by the CT scanner circuitry and used to generate an image of at least a portion of the body region of the subject.

2. The system of claim 1, wherein the radiation source electronically generates X-ray radiation.

3. The system of claim 1, wherein the fitted parameters are predetermined from scan data obtained by scanning phantoms on the CT imaging system, the phantoms being representative of a range of subject sizes.

4. The system of claim 1, wherein the third input is based on two-view scout image data of an area of interest for the subject.

5. The system of claim 1, wherein the at least one of the one or more processing units further cause the CT scanner circuitry to implement the acts of converting MDC to noise based on relationships defined by pixel noise and lesion size, and/or adjusting an automatic exposure control for the imaging system.

6. The system of claim 1, wherein the determined radiation dose has a greater than approximately 90 percent confidence level of identifying lesion targets of about 5 mm or greater in size.

7. The system of claim 1, wherein the determined radiation dose has a greater than approximately 93 percent confidence level of identifying lesion targets of about 5 mm or greater in-size.

8. A method for determining a minimum radiation dose for a computed tomography (CT) scanning device that includes CT scanner circuitry including one or more processing units, the method comprising the acts of:
   receiving in the CT scanner circuitry a first input indicative of a selected minimum detectable contrast;
   receiving in the CT scanner circuitry a second input indicative of an estimate of a size of a subject to be exposed to the radiation dose; and
   determining, via at least one of the one of more processing units, a minimum radiation dose to be applied via a radiation source of the CT scanning device, the minimum radiation dose being determined at least in part by a power law model relating the size of the subject, a lesion size, and a minimum detectable contrast, the power law model defined as $MDC=A(L)d^{B(L)}Dose^{C(L)}$, wherein (i) MDC is the selected minimum detectable contrast, (ii) d is lesion size, (iii) Dose is radiation dose, (iv) A(L), B(L), and C(L) are pre-determined fitted parameters for the CT scanning device, and (v) L is the estimate of the size of the subject.

9. The method of claim 8, wherein the fitted parameters are predetermined from scan data obtained by scanning phantoms on the CT scanning device, the phantoms being representative of a range of subject sizes.

10. The method of claim 8, wherein second input indicative of the estimate of the size of the subject is based on two-view scout image data of an area of interest for the subject.

11. The method of claim 8, wherein the CT scanning device is a Siemens Sensation 64, and/or the fitted parameters are approximated as A(L)=1.29 exp(0.09L), B(L)=−0.99, and C(L)=−0.36-0.06 exp(0.04L), with MDC expressed as a percentage, d expressed in millimeters, Dose expressed in milligrays, and L expressed in centimeters.

12. The method of claim 11, further comprising:
   converting MDC to noise according to the relationship defined by $$MDC\% = \frac{0.3N_p}{d},$$

wherein $N_p$ is pixel noise and d is lesion size; and/or adjusting an automatic exposure control for the CT scanning device.

13. The method of claim 8, wherein the CT scanning device is a GE Discovery HD750, and/or the fitted parameters are approximated as A(L)=13.95−11.21 exp(−(0.045L)$^{5.73}$), B(L)=0.00059 cos h(0.49L−10.89)−1.11, and C(L)=−0.49), with MDC expressed as a percentage, d expressed in millimeters, Dose expressed in milligrays, and L expressed in centimeters.

14. The method of claim 13, further comprising:
converting MDC to noise according to the relationship defined by MDC %=$0.253N_p/d$ wherein $N_p$ is pixel noise and d is lesion size; and/or
adjusting an automatic exposure control for the CT scanning device.

15. The method of claim 8, further comprising converting MDC to noise based on relationships defined by pixel noise and lesion size.

16. The method of claim 8, wherein the determined minimum radiation dose to be applied via the radiation source is electronically generated X-ray radiation.

17. The method of claim 8, wherein the determined radiation dose has a greater than approximately 90 percent confidence level of identifying lesion targets of about 5 mm or greater in size.

18. The method of claim 8, wherein the determined radiation dose has a greater than approximately 93 percent confidence level of identifying lesion targets of about 5 mm or greater in size.

19. A method for determining a radiation dose for a computed tomography (CT) scanning device that includes CT scanner circuitry including one or more processing units, the method comprising the acts of:
receiving in the CT scanner circuitry a first input of scout view image data;
determine, via at least one of the one or more processing units, a subject size from the received scout view image data;
placing a plurality of radiolucent dosimeters on an exterior surface of the subject;
apply a dose of radiation to the subject via a radiation source of the CT scanning device;
determining, via at least one of the one or more processing units, a peripheral radiation dose, $Dose_p$, based upon the exposure of at least one of the plurality of dosimeters to the applied dose of radiation; and
determining, via at least one of the one or more processing units, a patient specific weighted dose and/or center dose to which the subject has-been exposed according to the relationships defined by the following equations:

$$Dose_c = \frac{2r}{3-r}Dose_p \text{ and } Dose_w = \frac{2}{3-r}Dose_p,$$

wherein $Dose_c$ is the center dose, $Dose_w$ is the weighted dose, and $$r = \frac{Dose_c}{Dose_w},$$

and wherein a value for r is obtained for different subject sizes from a predetermined Gaussian relationship between r and equivalent subject diameters.

20. The method of claim 19, wherein the radiolucent dosimeters are calibrated using ion chambers in phantoms.

21. The method of claim 19, wherein the equivalent subject diameter and the ratio, r, is approximated by an inverse linear relationship.

* * * * *